United States Patent [19]

Miyata et al.

[11] Patent Number: 5,004,582

[45] Date of Patent: Apr. 2, 1991

[54] BIOCHEMICAL ANALYSIS APPARATUS

[75] Inventors: Yukihide Miyata; Hideo Ishizaka, both of Kanagawa; Yoshio Saito, Saitama; Takashi Koizumi, Kanagawa, all of Japan

[73] Assignee: Fuji Photo Film Co., Ltd., Kanagawa, Japan

[21] Appl. No.: 219,027

[22] Filed: Jul. 14, 1988

[30] Foreign Application Priority Data

| Jul. 15, 1987 | [JP] | Japan | 62-176563 |
| Feb. 10, 1988 | [JP] | Japan | 63-29842 |
| Mar. 19, 1988 | [JP] | Japan | 63-66354 |

[51] Int. Cl.$^5$ .............. G01N 33/48; G01N 33/50; G01N 35/04
[52] U.S. Cl. ........................ 422/56; 422/57; 422/65; 422/66; 422/67; 422/82.05; 62/132; 62/271
[58] Field of Search .......... 422/56, 57, 65, 66, 422/67, 82.05; 62/271, 132

[56] References Cited

U.S. PATENT DOCUMENTS

| 3,728,081 | 4/1973 | Bidanset | 422/66 |
| 3,904,369 | 9/1975 | Adler et al. | 422/66 |
| 3,923,463 | 12/1975 | Bagshawe et al. | 422/66 |
| 3,979,181 | 9/1976 | Plakas | 422/66 |
| 4,071,315 | 1/1978 | Chateau | 436/518 |
| 4,298,570 | 11/1981 | Lillig et al. | 422/65 |
| 4,421,719 | 12/1983 | Burleigh | 422/66 |
| 4,483,823 | 11/1984 | Umetsu et al. | 422/63 |
| 4,636,477 | 1/1987 | Rönka et al. | 422/66 |
| 4,720,372 | 1/1988 | Fey et al. | 422/67 |
| 4,924,714 | 5/1990 | Gross | 422/66 |
| 4,954,319 | 9/1990 | Koizumi et al. | 422/66 |
| 4,959,976 | 10/1990 | Matsuda et al. | 422/66 |

FOREIGN PATENT DOCUMENTS

| 2852944 B1 | 7/1978 | Fed. Rep. of Germany . |
| 53-21677 | 7/1978 | Japan . |
| 55-164356 | 12/1980 | Japan . |
| 0013162 | 1/1986 | Japan | 422/82.05 |
| 0134258 | 5/1989 | Japan | 422/82.05 |
| WO87/02122 | 4/1987 | PCT Int'l Appl. . |

Primary Examiner—Robert J. Hill, Jr.
Assistant Examiner—Kimberly A. Trautman
Attorney, Agent, or Firm—Sughrue, Mion, Zinn, Macpeak & Seas

[57] ABSTRACT

A biochemical analysis apparatus comprises a sample accommodating region, a refrigerator for keeping cool a long test film containing a reagent which reacts with a liquid sample to give rise to a change in optical density, and a test film conveyor for sequentially pulling out the long test film from the refrigerator. A sample applicator takes up the liquid sample from the sample accommodating region and applies it to the long test film at the position to which the long test film has been pulled out of the refrigerator. An incubator maintains the sample-applied portion of the long test film at a predetermined temperature for a predetermined time. A detector irradiates light to the sample-applied portion of the long test film, and measures the optical density given rise to by the reaction during or after the passage of the predetermined time.

13 Claims, 17 Drawing Sheets

BIOCHEMICAL ANALYSIS APPARATUS

BACKGROUND OF THE INVENTION

1. Field of the Invention

This invention relates to a biochemical analysis apparatus for applying a liquid sample to a test film provided with a single reagent layer or a plurality of reagent layers, maintaining the test film at a predetermined temperature (i.e. carrying out incubation) for a predetermined time, and measuring the degree of color formation given rise to by a reaction of the reagent with the liquid sample during or after the incubation. This invention particularly relates to a biochemical analysis apparatus which utilizes a long tape-like test film and enables storage of an unused portion of the long tape-like test film for a long period in the case where the overall test film has not been used at one time for the measurement. This invention also relates to a refrigerator for the biochemical analysis apparatus.

2. Description of the Prior Art

Qualitative or quantitative analysis of a specific chemical constituent in a liquid sample is generally conducted for various industrial purposes. Particularly, it is very important in biochemical and clinical fields to quantitatively analyze chemical constituents or physical constituents in body fluid such as blood or urine.

In recent years, as disclosed in, for example, Japanese Patent Publication No. 53(1978)-21677 and Japanese Unexamined Patent Publication No. 55(1980)-164356, there has been developed and put into practice a dry type chemical analysis slide for quantitatively analyzing a specific chemical constituent or a specific physical constituent contained in a liquid sample simply by applying a droplet of the liquid sample. With the chemical analysis slide, it is possible to analyze a liquid sample more simply and more quickly than with the conventional wet type analysis method. Therefore, the use of the chemical analysis slide is desirable particularly in medical organizations, research laboratories, or the like where many samples are to be analyzed.

In order to analyze a chemical constituent or the like contained in a liquid sample by use of the chemical analysis slide, a measured amount of the liquid sample is put on the chemical analysis slide and is maintained at a predetermined temperature (i.e. incubated) for a predetermined time in an incubator to cause a color reaction. The chemical analysis slide is then exposed to measuring light having a wavelength selected in advance in accordance with the combination of the constituent of the liquid sample with a reagent contained in the reagent layer of the chemical analysis slide, and the light reflected by the chemical analysis slide is measured in terms of the optical density. In this manner, it is possible to achieve quantitative analysis of the chemical constituent or the like.

In the medical organizations, research laboratories or the like in which many liquid samples are to be analyzed, it is desirable that the analysis be conducted automatically and sequentially. To satisfy this need, there have been proposed various chemical analysis apparatuses for carrying out sample analysis automatically and sequentially by use of the aforesaid chemical analysis slides. One of such chemical analysis apparatuses is disclosed in, for example, Japanese Unexamined Patent Publication No. 56(1981)-77746. Also, as a means for analyzing liquid samples automatically and sequentially, there has been proposed in, for example, U.S. Pat. No. 3,526,480 an apparatus wherein a long tape-like test film containing a reagent is accommodated instead of the aforesaid chemical analysis slides, and sample application, incubation and measurement are carried out sequentially by pulling out the test film.

With the technique wherein a single chemical analysis slide is used for a single measurement, many chemical analysis slides must be processed for automatically and sequentially carrying out the analysis of liquid samples, and therefore the apparatus becomes complicated, large and expensive. On the other hand, the technique wherein the long tape-like test film is used is advantageous for carrying out measurement automatically and sequentially. However, in general, the test film readily deteriorates with the passage of time. Therefore, in the case where the overall test film is not used for the measurement and a portion thereof remains unused, it is necessary for the unused portion of the test film to be ejected together with the used portion thereof from the chemical analysis apparatus and, for example, thrown away. Thus the test film cannot be used efficiently.

SUMMARY OF THE INVENTION

The primary object of the present invention is to provide a biochemical analysis apparatus which is made simple, small and cheap by employing the system utilizing a long tape-like test film advantageous for carrying out measurement automatically and sequentially, and which stores a remaining unused portion of the test film so that the remaining unused portion is usable for the next measurement in the case where the film portion remains unused after a series of measurements have been carried out.

Another object of the present invention is to provide a refrigerator for a biochemical analysis apparatus, wherein ambient air is prevented as much as possible from entering the refrigerator when a cassette which is accommodated in the refrigerator and whose long test film for biochemical analysis has been used is exchanged with a new long test film cassette for biochemical analysis, whereby long test films accommodated in the other cassettes in the refrigerator are prevented from deteriorating with the cassettes exposed to the ambient high-temperature, highhumidity atmosphere, and the cooling efficiency in the refrigerator is improved.

The specific object of the present invention is to provide a refrigerator for a biochemical analysis apparatus wherein cassettes housing long test films for biochemical analysis having different characteristics and/or cartridges housing biochemical analysis slides having different characteristics are accommodated, the temperature and humidity conditions in the respective compartments of the refrigerator are adjusted by a simple method in accordance with the characteristics of the long test films or the slides, and the refrigerating efficiency is improved as a whole.

The present invention provides a biochemical analysis apparatus comprising:

i) a sample accommodating means for accommodating a liquid sample, ii) a test film accommodating means for accommodating a long test film containing a reagent which reacts with said liquid sample to give rise to a change in optical density, and controlling an unused portion of said long test film at a predetermined temperature and humidity, iii) a test film conveyance means for sequentially pulling out said long test film accommodated in said test film accommodating means, iv) a sample application means for taking up said liquid sample accommodated in said sample accommodating means and applying a predetermined amount of said liquid sample onto said long test film at the position to which said long test film has been pulled out of said test film accommodating means, v) an incubator for maintaining the sample-applied portion of said long test film at a predetermined temperature for a predetermined time, and vi) a detection means for irradiating light to said sample-applied portion of said long test film and measuring the optical density given rise to by said reaction during or after the passage of said predetermined time.

The present invention also provides a first refrigerator for a biochemical analysis apparatus, wherein a plurality of cassettes housing long test films for biochemical analysis are accommodated in parallel, the refrigerator comprising:

i) a main body having a heat insulating configuration, and ii) a plurality of cover members divided from one another in the direction of the row of said cassettes, said cover members being openable and closeable independently of one another and having heat insulating configurations.

The present invention further provides a second refrigerator for a biochemical analysis apparatus, wherein a plurality of cassettes housing long test films for biochemical analysis and/or a plurality of cartridges housing biochemical analysis slides are accommodated, the refrigerator comprising:

i) outer walls having a heat insulating configuration, ii) at least one partition wall having large heat transfer effects for partitioning the area inward from said outer walls into at least two compartments, and iii) a cooling means associated with at least one of said compartments.

With the biochemical analysis apparatus in accordance with the present invention, the test film accommodating means for accommodating a long test film containing a reagent which reacts with the liquid sample to give rise to a change in optical density, and controlling an unused portion of the long test film at a predetermined temperature and humidity is provided. The long test film accommodated in the test film accommodating means is sequentially pulled out by the test film conveyance means, and the liquid sample accommodated in the sample accommodating means is taken up by the sample application means and applied onto the long test film at the position to which the long test film has been pulled out of the test film accommodating means. Thereafter, the sample-applied portion of the long test film is incubated, the optical density of the incubated portion of the long test film is measured by the detection means. Therefore, a change in the optical density produced by the color reaction can be measured automatically and sequentially, and the biochemical analysis apparatus can be made simple, small and cheap. Also, in the case where the long test film is not used over its overall length in a series of measurements and a film portion remains unused, the remaining unused portion of the test film can be stored in the biochemical analysis apparatus such that the remaining unused portion does not deteriorate and are usable for the next measurement.

With the first refrigerator for a biochemical analysis apparatus in accordance with the present invention, a plurality of cassettes housing the long test films for biochemical analysis can be accommodated in the refrigerator, and the floor space requirement can be reduced.

With the second refrigerator for a biochemical analysis apparatus in accordance with the present invention wherein the cassettes housing long test films for biochemical analysis having different characteristics and/or the cartridges housing biochemical analysis slides having different characteristics are accommodated in the refrigerator, the temperature and humidity conditions in the respective compartments of the refrigerator can be adjusted by a simple method in accordance with the characteristics of the long test films or the slides, and the refrigerating efficiency can be improved as a whole.

Also, with the first and second refrigerators for a biochemical analysis apparatus in accordance with the present invention, when a cassette which is accommodated in the refrigerator and whose long test film for biochemical analysis has been used is exchanged with a new long test film cassette for biochemical analysis, ambient air can be prevented from entering the refrigerator. Therefore, the other cassettes accommodated in the refrigerator can be prevented from exposure to the ambient high-temperature, high-humidity atmosphere, and the long test films accommodated in the other cassettes in the refrigerator can be prevented from deterioration. Also, the cooling efficiency in the refrigerator can be improved.

DESCRIPTION OF THE PREFERRED EMBODIMENTS

The present invention will hereinbelow be described in further detail with reference to the accompanying drawings.

Figure 1:
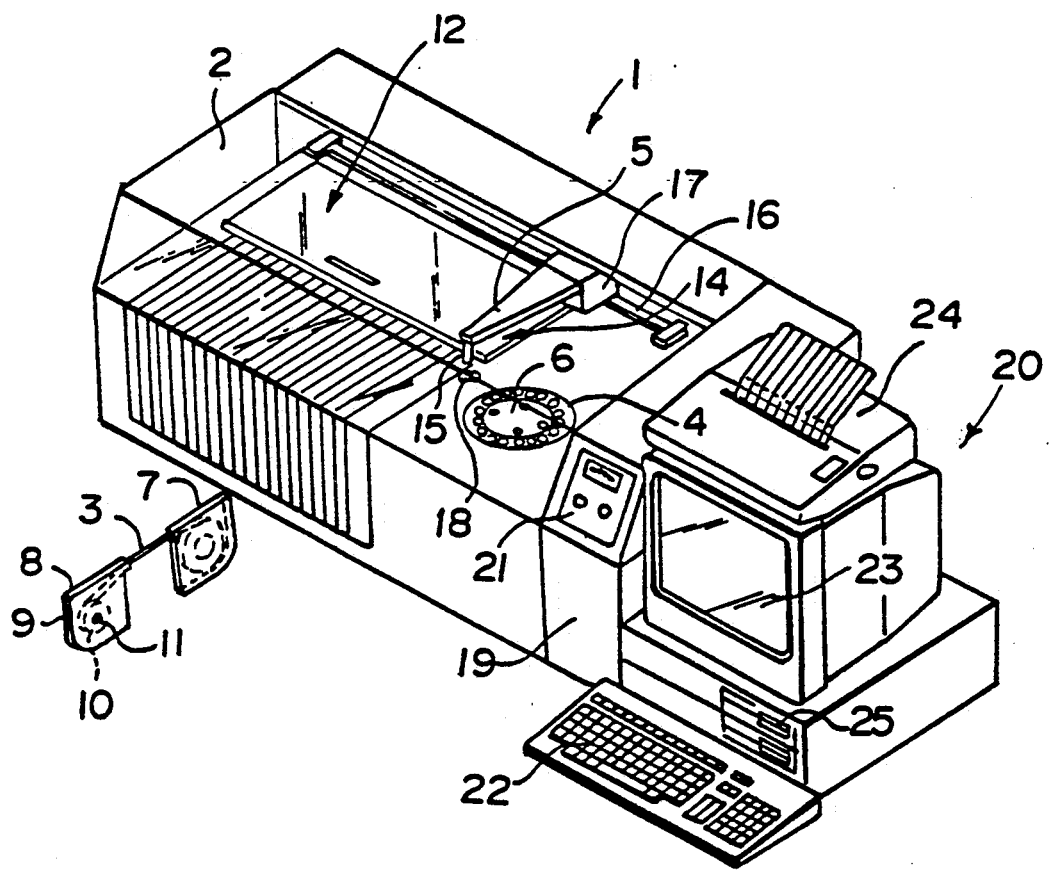
FIG. 1 is a perspective view showing an embodiment of the biochemical analysis apparatus in accordance with the present invention.

With reference to FIG. 1, a biochemical analysis apparatus 1 is provided with a transparent cover 2, and a liquid sample, a long tape-like test film 3 and the like are fed into and out of the apparatus 1 by opening the cover 2. The apparatus 1 is provided with a sample accommodating means 4 for accommodating a liquid sample such as blood serum or urine along a ring-like area, and the liquid sample is taken up from the sample accommodating means 4 and applied by a sample application means 5 as will be described later. A centrifugation means 6 is provided inward from the sample accommodating means 4 for accommodating body fluid, for example, blood (whole blood), and centrifuging the blood to produce blood serum as the liquid sample, and for other purposes. The long test film 3 contains a reagent undergoing a color reaction with only a specific chemical constituent or a specific physical constituent that is to be analyzed in the liquid sample, and many kinds of the long test films 3, 3, . . . are prepared in accordance with the measurement items. An unused portion of the long test film 3 which has not yet been used for measurement is wound up in a film feed cassette 7, and the used portion of the long test film 3 which has already been used for measurement is wound up in a film wind-up cassette 8. The lot number, film number, measurement item, working life and other information on the long test film 3 are indicated by, for example, a bar code 9, on one face of the film wind-up cassette 8. At the center of a reel 10 in the film wind-up cassette 8, a hole 11 is provided for engagement with a rotation shaft of a motor for pulling the long test film 3 out of the film feed cassette 7 after the long test film 3 has been accommodated in the biochemical analysis apparatus 1 as will be described later. The long test film 3 is accommodated in the biochemical analysis apparatus 1 in the form wound up in the film feed cassette 7 and the film wind-up cassette 8. As shown in FIG. 1, the film feed cassette 7 and the film wind-up cassette 8 are formed independently of each other. A test film accommodating means 12 accommodates unused portions of a plurality of the long test films 3, 3, . . . in parallel so that various items of measurements can be carried out simultaneously by use of the apparatus 1. At the right end of the test film accommodating means 12 in FIG. 1, an electrolyte determination slide accommodating region 14 is provided for accommodating electrolyte determination slides for determination of electrolytes such as $Na^+$, $K^+$ and $Cl^-$ in the liquid sample. The unused slides are stacked in the accommodating region 14. The sample application means 5 is provided with a sample applying nozzle 15 at the end, and is moved in the extending direction of a rail 16 by a movement means 17 placed on the rail 16 for taking up the liquid sample from the sample accommodating means 4 or the centrifugation means 6, and applying the liquid sample onto the long test film 3 pulled out by a test film conveyance means from the test film accommodating means 12 or onto the electrolyte determination slide pushed out of the electrolyte determination slide accommodating region 14. The movement means 17 also moves the sample application means 5 vertically. The sample application means 5 is kept at its upper position at the time it is moved by the movement means 17 in the extending direction of the rail 16, and is moved down at the time of taking out and application of the liquid sample and at the time of washing as will be described later.

In this specification, both the electrolyte determination slide and the long test film 3 are generically referred to as the test film.

After applying the liquid sample onto the test film, the sample applying nozzle 15 is washed at a nozzle washing region 18 provided close to the electrolyte determination slide accommodating region 14 and the sample accommodating means 4 therebetween in accordance with the operation sequence as will be described later, and is reused for sample application.

The test film on which the liquid sample has already been applied is incubated by an incubator as will be described later, and subjected to measurement by a measurement means.

Control of operations of the overall apparatus 1, processing of the measurement data and the like are carried out by a circuit region 19 and a computer 20 connected therewith. An operating and display region 21 on the front surface of the circuit region 19 is provided with a power source switch for the apparatus 1, an ammeter for monitoring the current consumption in the apparatus 1, and other members. The computer 20 is provided with a keyboard 22 for giving instructions to the apparatus 1, a CRT display device 23 for displaying the subsidiary information for instructions, measurement results and other items, a printer 24 for printing the measurement results, and a floppy disk drive unit 25 for accommodating a floppy disk for storage of commands for giving various instructions to the apparatus 1 and the information on the measurement results.

Figure 2:
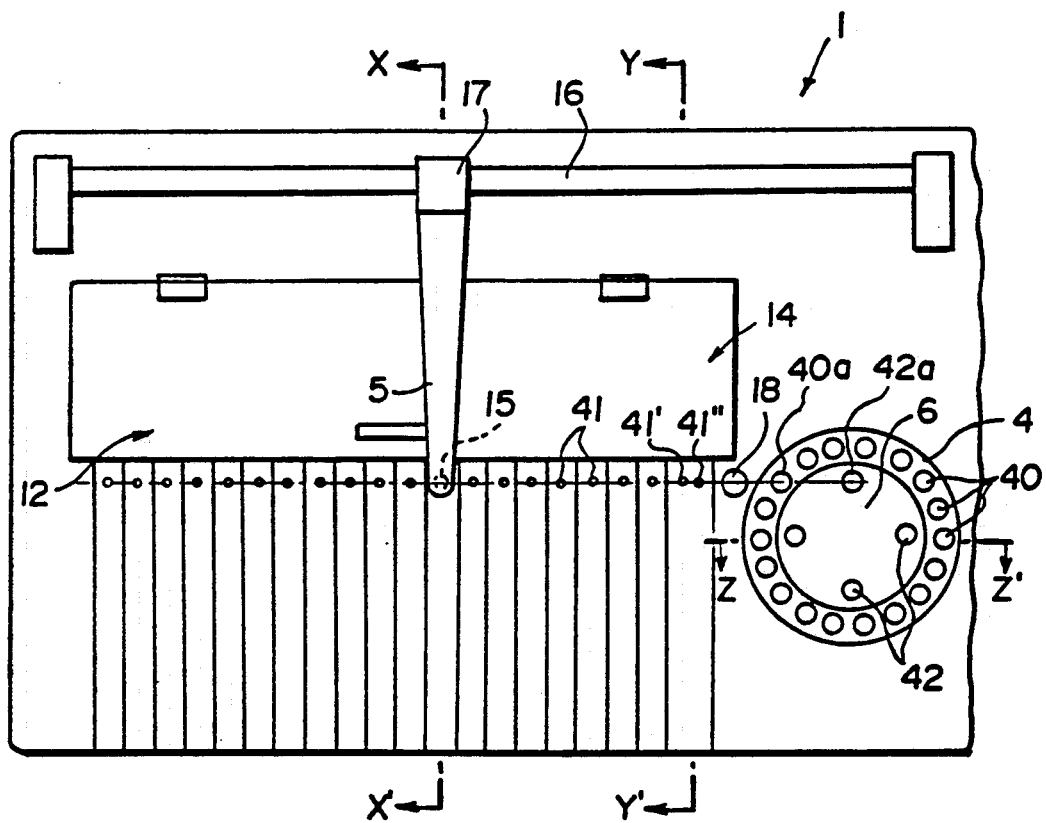
FIG. 2 is a plan view showing the major part of the embodiment shown in FIG. 1.

With reference to FIG. 2 showing the major part of the apparatus 1, the test film accommodating means 12 is constituted so that sample applying positions 41, 41, . . . , 41' and 41" for all of the test films pulled out or pushed out of the test film accommodating means 12 stand in a straight line indicated by the chain line. Also, the nozzle washing region 18, a liquid sample take-out position 40a in the sample accommodating means 4, and a liquid sample take-out position 42a in the centrifugation means 6 are disposed on said straight line. The arrangement on the straight line simplifies the configuration of the movement means as will be described later, which in turn contributes to a decrease in operation failures and cost of the apparatus 1.

The sample accommodating means 4 accommodates a plurality of liquid samples in accommodating regions 40, 40, . . . disposed in the ring-like area. The accommodating regions 40, 40, . . . are automatically rotated along the circular path until the liquid sample which is accommodated in one of the accommodating regions 40, 40, . . . and which is to be used for the next measurement arrives at the take-out position 40a. In order to prevent the liquid samples accommodated in the accommodating regions 40, 40, . . . from evaporating and deteriorating, a cover (not shown) is provided on the accommodating regions 40, 40, . . . outside of the take-out position 40a.

The centrifugation means 6 accommodates body fluid in accommodating regions 42, 42, . . . , and centrifuges it. Thereafter, as in the case of the sample accommodating means 4, the accommodating regions 42, 42, . . . are rotated until the liquid sample is located at the take-out position 42a in the sequence of take-out by the sample application means 5. By way of example, the body fluid is blood (whole blood). Upon centrifugation of the whole blood, blood plasma is separated up, and blood clot sediments. In this case, blood serum or blood plasma as the liquid sample can be taken up by the sample application means 5 without being separated into a vessel different from the vessel of blood clot. As in the case of the sample accommodating means 4, a cover (not shown) is provided on the accommodating regions 42, 42, . . . of the centrifugation means 6.

The sample application means 5 is moved by the movement means 17 in the extending direction of the rail 16, takes up the liquid sample from the take-out position 40a or the take-out position 42a, and applies it to the sample applying position 41 or 41' on the test film. Both the liquid sample and a reference solution should be applied to the electrolyte determination slide, and therefore the sample applying positions 41' and 41" are provided. The liquid sample is applied to the sample applying position 41', and the reference solution is applied to the sample applying position 41".

Figure 3:
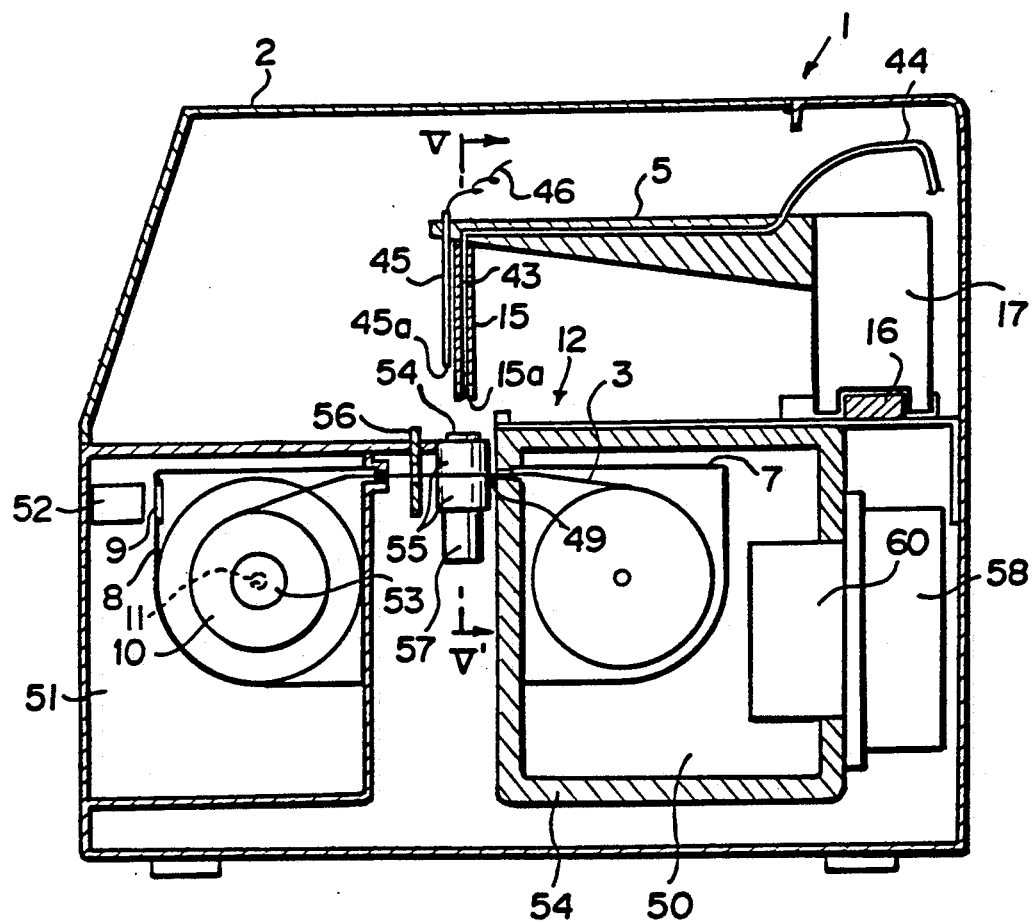
FIG. 3 is a sectional view taken along line X—X' of FIG. 2.

FIG. 3 is a sectional view taken along line X—X' of FIG. 2. In FIG. 3, similar elements are numbered with the same reference numerals with respect to FIGS. 1 and 2. With reference to FIG. 3, the long test film 3 is accommodated in the film feed cassette 7 and the film wind-up cassette 8 and is accommodated in this form in the apparatus 1. The film feed cassette 7 is accommodated in a refrigerator 50 which constitutes the test film accommodating means 12, and the film wind-up cassette 8 is accommodated in a wind-up chamber 51.

With the configuration wherein the unused portion of the long test film 3 is accommodated in the film feed cassette 7, the unused long test film 3 can be accommodated in the test film accommodating means 12 without the hands of the operator contacting the unused long test film 3.

As mentioned above, by way of example, the bar code 9 indicating the lot number, film number, measurement item, working life and other information on the long test film 3 is provided on one face of the film wind-up cassette 8. The information indicated by the bar code 9 is read by a bar code reading means 52 provided at a position in the wind-up chamber 51 corresponding to the position at which the bar code 9 is located when the film wind-up cassette 8 is accommodated in the wind-up chamber 51. The information thus read is stored on, for example, the floppy disk in the floppy disk drive unit 25 shown in FIG. 1, and is used for control of the measurement item and control of the length of the unused film portion remaining in the film feed cassette 7, and elimination of measurement errors caused by fluctuations among production lots of the long test films 3, 3, . . . Also, in the case where the long test film 3 is taken out of the apparatus 1 after being used partially, the film number, the length of the remaining unused film portion and other information on the long test film 3 are stored on the floppy disk unless a deletion command is entered from the keyboard 22 shown in FIG. 1 or until the information is deleted automatically at the time the long test film 3 runs out of the working life. When the long test film 3 is again accommodated in the test film accommodating means 12 for reuse, the film number of the long test film 3 is compared with the information stored on the floppy disk, and the length of the remaining unused portion of the long test film 3 and other items are controlled again.

The aforesaid bar code 9 may be provided on the film feed cassette 7, and the bar code reading means 52 may be provided inside of the refrigerator 50. Also, the means for transmitting the lot number, the working life and other information on the long test film 3 to the apparatus 1 is not limited to the bar code 9 and the means for reading the bar code 9, and any other known means for recording the information on the film feed cassette 7 or on the film wind-up cassette 8 and reading the information at the time the long test film 3 is accommodated in the apparatus 1 may be employed for this purpose.

The refrigerator 50 is enclosed by a refrigerator wall 54 composed of a heat insulating material. A cooling and dehumidifying device 58 for keeping the inside of the refrigerator 50 at a predetermined low temperature and low humidity is provided on one surface of the refrigerator wall 54, and air inside of the refrigerator 50 is circulated by a fan 60.

Figure 4:
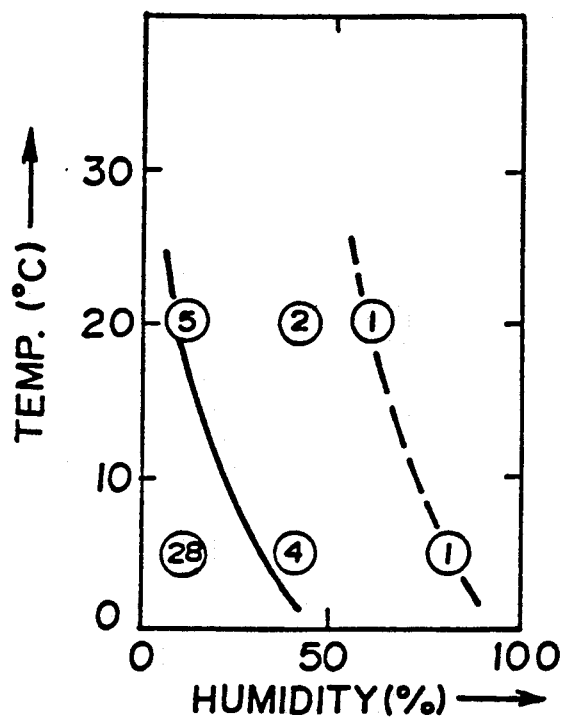
FIG. 4 is a graph showing the rates of deterioration of an unused long test film with the passage of time when the unused long test film is maintained under various temperature-humidity conditions, in terms of the number of days for which the long test film can be stored under such conditions without becoming unusable for measurement.

FIG. 4 shows the rates of deterioration of the unused long test film 3 with the passage of time when the unused long test film 3 is maintained under various temperature-humidity conditions, in terms of the number of days for which the long test film 3 can be stored under such conditions without becoming unusable for measurement. Each of the numerals indicated in the circles in FIG. 4 represents the number of days for which the long test film 3 can be stored under the temperature-humidity conditions corresponding to the circle without becoming unusable for measurement. The number of days for which the long test film 3 can be stored under the temperature-humidity conditions without becoming unusable for measurement increases sharply at the left bottom of the graph (under a low temperature, low humidity conditions) shown in FIG. 4. Therefore, the long test film 3 can be stored for a longer period in the apparatus 1 by accommodating the unused portion of the long test film 3 in the refrigerator 50 and maintaining the unused portion at a predetermined low temperature and low humidity adjusted by considering the working life and the working frequency of the long test film 3 and other items.

Reverting to FIG. 3, when the film wind-up cassette 8 is accommodated in the wind-up chamber 51, a rotation shaft of a test film wind-up motor 53 constituting the test film conveyance means for the long test film 3 provided in the wind-up chamber 51 engages with a hole 11 formed at the center of a reel 10 of the film wind-up cassette 8. As the motor 53 is rotated, the long test film 3 is pulled out of the film feed cassette 7 through a film outlet 49 of the refrigerator 50, and is wound up in the film wind-up cassette 8. As mentioned above, the film feed cassette 7 and the film wind-up cassette 8 are provided independently of each other. Therefore, the film outlet 49 of the refrigerator 50 may be as small as to allow the passage of the long test film 3 therethrough, and the cooling and dehumidifying efficiency in the refrigerator 50 can be maintained high. Also, the long test film 3 can also be used in various apparatuses among which the distance between the refrigerator 50 and the wind-up chamber 51 differs. Furthermore, with the configuration wherein the used portion of the long test film 3 is accommodated in the film wind-up cassette 8, the used long test film 3 on which the liquid sample has already been applied can be taken out of the apparatus 1 and discarded or processed for other purposes without the hands of the operator contacting the used long test film 3. For discarding the used long test film 3, a cutter for cutting the used film may be provided near the inlet of the wind-up chamber 51, and a box for receiving the cut film fragments and capable of being fitted to and removed from the apparatus 1 may be provided instead of the wind-up chamber 51. With this configuration, the used film contained in the box can be taken out of the apparatus 1 together with the box and discarded or processed for other purposes without the hands of the operator contacting the used film. In this case, conveyance of the test film may be carried out by the provision of conveying rollers for grasping and conveying the test film.

The exposed portion of the long test film 3 between the film feed cassette 7 and the film wind-up cassette 8 passes through an incubator 55 provided with a shutter 54 and between a light projector and a light receiver of a photoelectric switch 56. A measuring device 57 for measuring the optical density produced by a color reaction of the long test film 3 with the liquid sample is disposed under the incubator 55.

With the configuration illustrated in FIG. 3 wherein the refrigerator 50 and the incubator 55 are close to each other, the length of the portion of the long test film 3 pulled out of the film feed cassette 7 for a single measurement may be short so that more measurements can be achieved with the long test film 3 of the same length.

Figure 5:
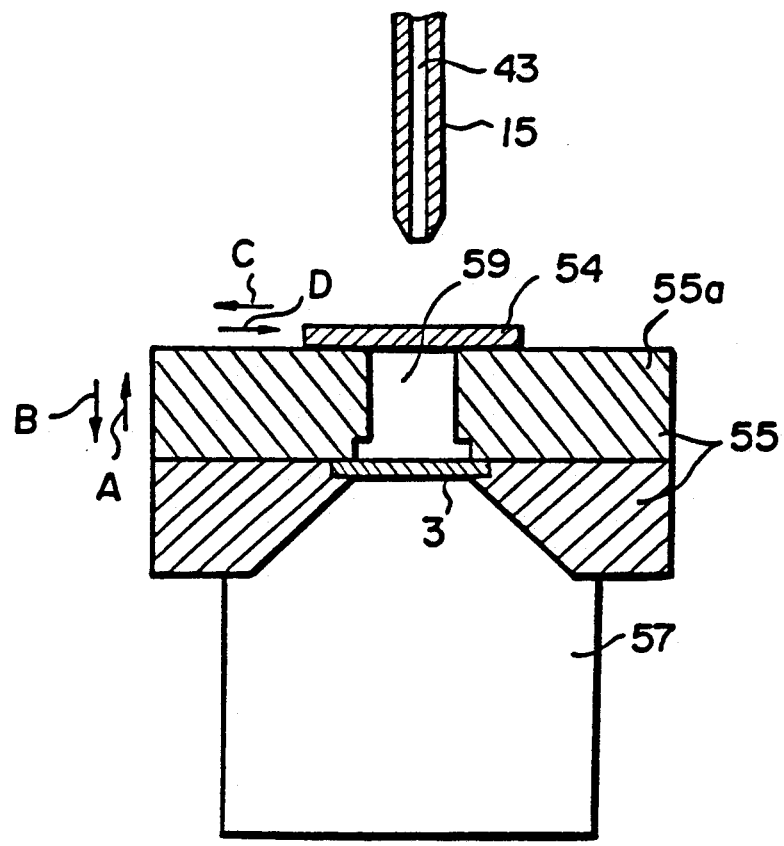
FIG. 5 is a sectional view taken along line V—V' of FIG. 3.

With reference to FIG. 5 illustrating the configuration of the incubator 55 along line V—V' of FIG. 3, the long test film 3 is pulled out of the film feed cassette 7 and intermittently moved from the rear of the drawing sheet in FIG. 5 to the front thereof. Prior to this step, an upper cover 55a of the incubator 55 has been moved in the direction as indicated by the arrow A. After the long test film 3 has been moved as mentioned above, the upper cover 55a is moved in the direction as indicated by the arrow B, and pushes down the long test film 3 as illustrated. Then, the shutter 54 is moved in the direction as indicated by the arrow C, the sample application means 5 is moved down to apply the liquid sample from the sample applying nozzle 15 onto the long test film 3 through a hole 59. Thereafter, the shutter 54 is moved in the direction as indicated by the arrow D to close the hole 59 as illustrated and prevent air flow between the inside and outside of the hole 59, and the incubator 55 incubates so that the temperature in the inside thereof reaches a predetermined value, for example, 37° C. In the course of the incubation or after the incubation is finished, the optical density at the portion of the long test film 3 on which the liquid sample has already been applied is measured by the measuring device 57. Instead of providing the shutter 54, the upper cover 55a of the incubator 55 may be constituted moveable in the directions as indicated by the arrows C and D as well as in the directions as indicated by the arrows A and B. In this case, the upper cover 55a of the incubator 55 need not be provided with the hole 59 for sample application. But instead, after the liquid sample has been applied onto the long test film 3 by moving the upper cover 55a in the direction as indicated by the arrow C, the upper cover 55a may be moved to its original position in the direction as indicated by the arrow D, and incubation may then be carried out.

With this embodiment wherein the sample application, incubation and measurement are carried out at a single position, the position to which the liquid sample has been applied is incubated and measured reliably even though the accuracy of feed of the long test film 3 by the test film wind-up motor 53 is low. Also, since the sample applying position 41 (as shown in FIG. 2) with respect to the incubator 55 is always constant, the temperature distribution inside of the incubator 55 is constant, the color reaction is effected under constant conditions, and the measurement accuracy becomes high. Furthermore, in the case where the sample application, incubation and measurement are carried out at different positions, it is necessary for the rotation of the motor 53 to be controlled each time the long test film 3 is to be moved from the sample applying position to the incubating position or from the incubating position to the measuring position. However, with the aforesaid embodiment wherein the sample application, incubation and measurement are carried out at a single position, such complicated control is not required.

The photoelectric switch 56 shown in FIG. 3 detects holes or marks of the long test film 3. Based on the signal generated by the photoelectric switch 56, the long test film 3 is pulled out of the film feed cassette 7 by a length necessary for a single measurement. The computer 20 shown in FIG. 1 counts the number of pull-out operations of the long test film 3, and issues a warning, for example, by sound or light, to the operator when the length of the remaining unused portion of the long test film 3 has decreased to a predetermined value or less. Also, a hole or a mark discriminable by the photoelectric switch 56 from the holes or marks provided at the predetermined measurement length intervals on the long test film 3 is provided near the tail edge portion of the long test film 3. When the hole or mark near the tail edge portion of the long test film 3 is detected, the photoelectric switch 56 produces a signal for stopping the pull-out of the long test film 3. The end of the long test film 3 may be judged on the basis of only the value counted by the computer 20. However, the end mark or the like should preferably be provided on the long test film 3 itself to cope with the case wherein the long test film 3 is taken out of the apparatus 1 after it has partially been used for measurement, and is artificially wound up slightly and then loaded to the apparatus 1 again.

An elongated pipe 43 continuing into a leading end 15a of the sample applying nozzle 15 is provided in the sample application means 5. The pipe 43 is communicated with a flexible pipe 44 so that the liquid sample is fed through the pipes 43 and 44 into the sample application means 5 and applied onto the test film as will be described later. The reference solution is fed and washing liquid is delivered through the pipes 43 and 44.

A liquid level detector 45 is provided in parallel with the sample applying nozzle 15 in the vicinity thereof. The liquid level detector 45 is provided so that its leading edge 45a is slightly (for example, by approximately 2.5 mm) higher than the leading edge 15a of the sample applying nozzle 15. When the sample application means 5 is moved down by the movement means 17 for taking up the liquid sample accommodated in the sample accommodating means 4 or the centrifugation means 6, the leading edge 15a of the sample applying nozzle 15 enters the liquid sample, and the leading edge 45a of the liquid level detector 45 contacts the liquid sample. At this time, a signal indicating that the leading edge 45a of the liquid level detector 45 has contacted the liquid sample is produced by the liquid level detector 45, and transmitted to the circuit region 19 shown in FIG. 1 through a signal line 46. Based on the signal, the downward movement of the sample application means 5 is stopped. In this manner, the leading edge 15a of the sample applying nozzle 15 can be entered into the liquid sample up to a predetermined depth from the surface of the liquid sample regardless of the amount of the liquid sample.

Figure 6:
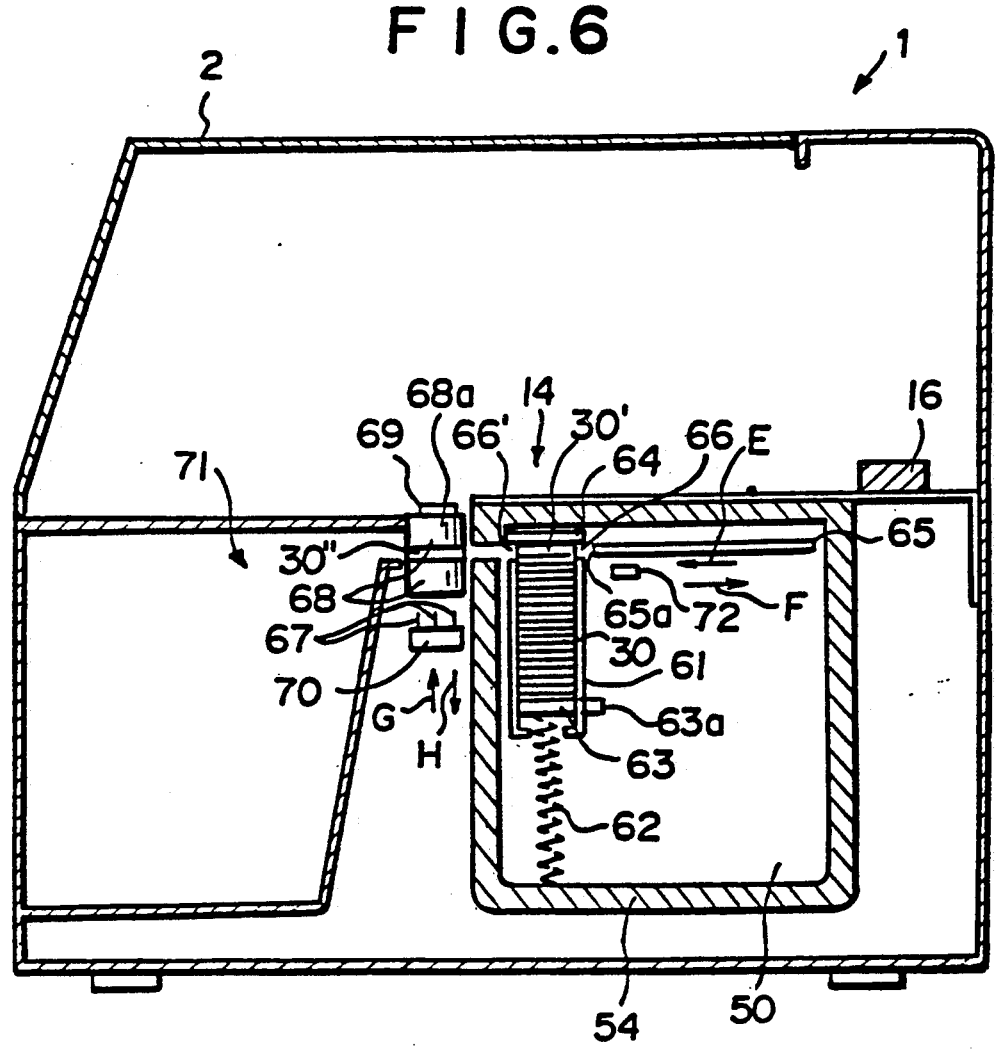
FIG. 6 is a sectional view taken along line Y—Y' of FIG. 2.

With reference to FIG. 6 illustrating the configuration of the electrolyte determination slide accommodating region 14 along line Y—Y' of FIG. 2, electrolyte determination slides 30, 30, . . . are stacked in a slide magazine 61, and a bottom plate 63 of the slide magazine 61 is urged up by a spring 62. The top slide 30' among the electrolyte determination slides 30, 30, . . . is pushed up against a top plate 64 of the slide magazine 61. A slide conveying member 65 constituting the test film conveyance means for the slides 30, 30, . . . is moveable by a drive means (not shown) in the directions as indicated by the arrows E and F. As the slide conveying member 65 is moved in the direction as indicated by the arrow E, a leading edge 65a thereof enters a slit 66 formed in the slide magazine 61, and pushes the top slide 30' in the slide magazine 61. As a result, the slide 30' is pushed out of the slide magazine 61 through a slit 66' into an incubator 68 as indicated by a reference numeral 30". At the incubator 68, a shutter 69 is opened, a sample liquid is applied to the slide 30", the shutter 69 is then closed, and the slide 30" is incubated. Thereafter, a measuring device 70 is moved up in the direction as indicated by the arrow G until potential measuring probes 67, 67, 67 contact electrodes (not shown) of the slide 30" in the incubator 68, and a difference in potential is measured. Thereafter, the measuring device 70 is moved in the direction as indicated by the arrow H to its waiting position as shown in FIG. 6. The incubator 68 has nearly the same configuration as the incubator 55 for the long test film 3 shown in FIG. 5, except that the slide 30' pushed out by the slide conveying member 65 can be accommodated as the slide 30", and the liquid sample and the reference solution can be applied to the predetermined positions on the slide 30". Also, instead of providing the measuring device 57 shown in FIG. 5, the probes 67, 67, 67 of the measuring device 70 moved in the direction as indicated by the arrow G in FIG. 6 contact the predetermined electrodes to measure a difference in potential.

As in the case of the long test film 3, instead of providing the shutter 69, the effect of the shutter 69 may be achieved by an upper cover 68a of the incubator 68. Also, since the sample application, incubation and measurement are carried out at a single position, the same effects as in the case of the long test film 3, such as simplification of the control of push-out of the slide 30' by the slide conveying member 65 and improved measurement accuracy, can be obtained.

After the measurement is finished, the slide 30" is pushed by the slide conveying member 65 leftward in FIG. 6 into a slide discarding region 71. The slide conveying member 65 is then moved in the direction as indicated by the arrow F to the waiting position shown in FIG. 6.

As the slides 30, 30, . . . are pushed one by one out of the slide magazine 61, the bottom plate 63 of the slide magazine 61 is pushed up by the spring 62. At the time a protrusion 63a projecting from the bottom plate 63 out of the slide magazine 61 faces a proximity switch 72, a warning is issued to the operator to instruct replenishment of slides 30, 30, . . . In the case where a predetermined number of the slides 30, 30, . . . are then pushed out of the slide magazine without new slides replenished and the slide magazine 61 runs out of the slide 30 while the liquid sample to be measured for a difference in potential is still present, the apparatus 1 is stopped without sample application and other operations for measurement of the liquid sample being carried out.

Figure 7:
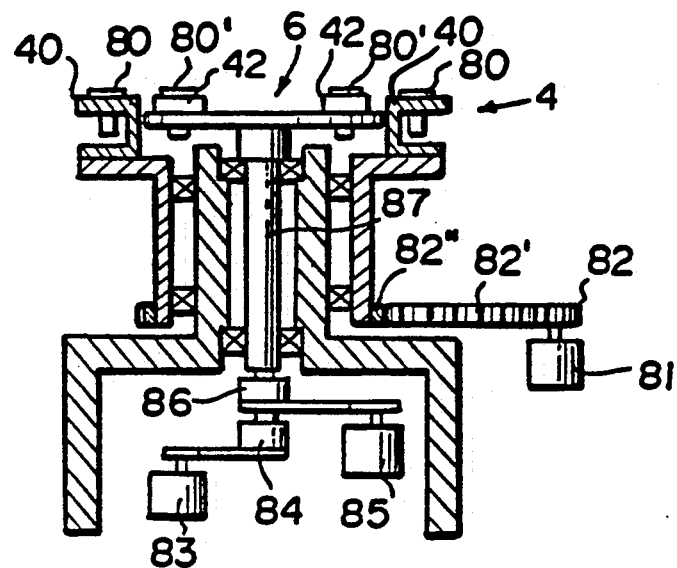
FIG. 7 is a sectional view taken along line Z-Z' of FIG. 2.

With reference to FIG. 7 illustrating the sample accommodating means 4 and the centrifugation means 6 along line Z—Z' of FIG. 2, the sample accommodating means 4 is constituted so that sample cups 80, 80, . . . for containing the liquid samples are placed in the accommodating regions 40, 40, . . . provided in the ring-like area on the upper surface of the sample accommodating means 4, and the overall sample accommodating means 4 is rotated by a motor 81 via gears 82, 82' and 82". The operation of the motor 81 is controlled so that the liquid samples are located one after another at the liquid sample take-out position 40a shown in FIG. 2 in the sequence of take-out from the sample accommodating means 4 and sample application.

Sample cups 80', 80', . . . containing body fluid are placed in the accommodating regions 42, 42, . . . on the upper surface of the centrifugation means 6. From the viewpoint of cup control and reduction in cost, cups of the same type as the sample cups 80, 80, . . . on the sample accommodating means 4 are employed as the sample cup 80', 80', . . .

A motor 83 is provided for centrifugation. A motor 85 rotates the sample cups 80', 80', . . . to locate the liquid sample (body fluid) after centrifugation at the liquid sample take-out position 42a shown in FIG. 2 as in the case of the motor 81.

At the time centrifugation is to be carried out, a clutch 86 is disengaged to disconnect the motor 85 from a rotation shaft 87, and a clutch is engaged to transmit the power of the motor 83 to the rotation shaft 87. The motor is operated in this condition to rotate the sample cups 80', 80', . . . at a high speed with the bottoms of the sample cups 80', 80', . . . facing outward and openings thereof facing inward by the centrifugal force so that the body fluid does not spill out of the sample cups 80', 80', . . . After centrifugation is thus carried out for a predetermined time, the clutch 84 is disengaged to disconnect the motor 83 from the rotation shaft 87, and the clutch 86 is engaged to connect the motor 85 to the rotation shaft 87. The motor 85 is then operated to rotate the sample cups 80', 80', . . . until the liquid sample (body fluid) after centrifugation is located at the liquid sample take-out position 42a shown in FIG. 2.

As the centrifugation means 6 is provided in the space inward from the sample accommodating means 4, the overall apparatus 1 can be made small. Also, since the accommodating regions 42, 42, . . . of the centrifugation means 6 are provided inward from the accommodating regions 40, 40, . . . arranged in the ring-like area of the sample accommodating means 4, feed of the liquid sample (body fluid) to the apparatus 1 for measurement can be carried out at a single position, and therefore a high operating efficiency can be obtained.

Figure 8:
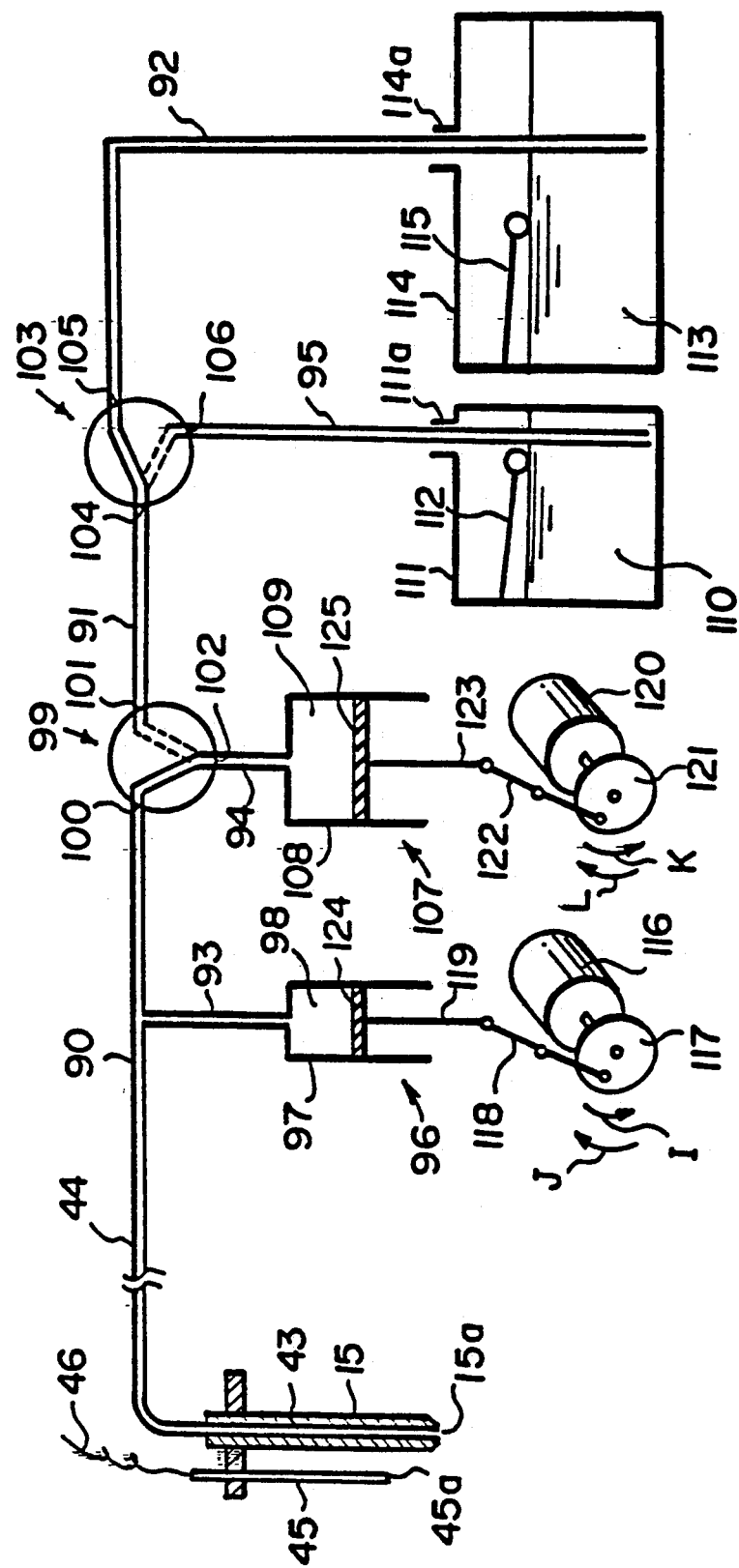
FIG. 8 is a flow diagram showing the pipes communicating with a pipe of a sample application nozzle.

With reference to FIG. 8 showing the pipes communicating with the pipe 43 passing through the center of the sample applying nozzle 15 of the sample application means 5, the pipe 43 communicates with the flexible pipe 44 which communicates with an end of a pipe 90. The pipe 90 communicates at its intermediate point with a pipe 93 communicating with a space 98 in a cylinder 97 of a suction and delivery means 96, and the other end of the pipe 90 is connected to a port 100 of a solenoid valve 99. A pipe 91 connects a port 101 of the solenoid valve 99 with a port 104 of a solenoid valve 103. A port 102 of the solenoid valve 99 is connected to a pipe 94 communicating with a space 109 in a cylinder 108 of a suction and delivery means 107. The solenoid valve 99 is changed over by a signal received from the exterior to communicate the pipes 90 and 94 with each other and disconnect the pipe 91 from the pipe 94, or conversely to communicate the pipes 91 and 94 with each other and disconnect the pipe 90 from the pipe 94. A port 106 of the solenoid valve 103 is connected to an end of a pipe 95 having the other end extending to the vicinity of the bottom of a tank 111 via an opening 111a of the tank 111 and immersed in a reference solution 110 in the tank 111. A liquid level detector 112 is provided in the tank 111 for detecting the level of the reference solution 110 in the tank 111. A signal indicating the level of the reference solution 110 is transmitted to the circuit region 19 shown in FIG. 1 via a signal line (not shown), and a warning is issued by, for example, sound or light, to the operator when the level of the reference solution 110 is low. A port 105 of the solenoid valve 103 is connected to an end of a pipe 92 having the other end extending to the vicinity of the bottom of a tank 114 via an opening 114a of the tank 114 and immersed in a washing liquid 113 in the tank 114. As in the case of the tank 111, a liquid level detector 115 is provided in the tank 114. The solenoid valve 103 is changed over by a signal received from the exterior to communicate the pipes 91 and 92 with each other and disconnect the pipe 91 from the pipe 95, or conversely to communicate the pipes 91 and 95 with each other and disconnect the pipe 91 from the pipe 92.

The suction and delivery means 96 sucks the liquid sample from the leading edge 15a of the sample applying nozzle 15, and applies it therefrom onto the test film. In order to sucks the liquid sample, the leading edge 15a of the sample applying nozzle 15 is entered into the liquid sample accommodated in the sample accommodating means 4 or the centrifugation means 6 until the leading edge 45a of the liquid level detector 45 contacts the surface of the liquid sample, and the solenoid valve 99 is controlled so that the pipes 90 and 94 disconnect from each other and the pipes 91 and 94 communicate with each other. In this condition, the motor 116 is rotated in the direction as indicated by the arrow I, the rotation force is converted into linear motion via a cam plate 117 and a link mechanism 118, and the linear motion is transmitted to a piston rod 119. As a result, the piston rod 119 is moved down to pull a piston 124 down and broaden a space 98 inside of the cylinder 97. In this manner, the liquid sample is moved from the leading edge 15a of the sample applying nozzle 15 to the pipes 43, 44 and 90. In order to apply the liquid sample onto the test film, the sample application means 5 is moved to the sample applying position of the test film, the shutter 54 or the shutter 69 is opened, the sample applying nozzle 15 is moved down, and then the motor 116 is rotated in the direction as indicated by the arrow J. As a result, the drive force of the motor 116 is transmitted to the piston rod 119 via the cam plate 117 and the link mechanism 118, the piston rod 119 is moved up to push the piston 124 up, and the liquid sample is applied in an amount corresponding to the extent of the movement of the piston 124.

In order to deliver the reference solution 110 from the leading edge 15a of the sample applying nozzle 15, the solenoid valve 99 is first controlled so that the pipes 91 and 94 communicate with each other and the pipes 90 and 94 are disconnected from each other, and the solenoid valve 103 is controlled so that the pipes 91 and 95 communicate with each other and the pipes 91 and 92 are disconnected from each other. In this condition, the motor 120 is rotated in the direction as indicated by the arrow K, the rotation force is converted into linear motion via a cam plate 121 and a link mechanism 122, and the linear motion is transmitted to a piston rod 123. As a result, the piston rod 123 is moved down to pull a piston 125 down and broaden a space 109 inside of the cylinder 108. In this manner, the reference solution 110 is moved through the pipe 95, the solenoid valve 103, the pipe 91, the solenoid valve 99 and the pipe 94 into the space 109 in the cylinder 108. Then, the solenoid valve 99 is controlled so that the pipes 90 and 94 communicate with each other and the pipes 91 and 94 are disconnected from each other. Thereafter, the motor 120 is rotated in the direction as indicated by the arrow L to move the piston rod 123 up and push the piston 125 up, and the reference solution 110 is delivered from the leading edge 15a of the sample applying nozzle 15 in an amount corresponding to the extent of movement of the piston 125.

Delivery of the washing liquid 113 from the leading edge 15a of the sample applying nozzle 15 is controlled in the same manner as the delivery of the reference solution 110, except that the solenoid valve 103 is controlled so that the pipes 91 and 92 communicate with each other and the pipes 91 and 95 are disconnected from each other when the washing liquid 113 is to be moved to the space 109 in the cylinder 108.

With the aforesaid pipe connections, the sample applying nozzle 15 works for both the liquid sample and the reference solution, and it is not necessary to use dual nozzles as disclosed in, for example, Japanese Unexamined Patent Publication No. 61(1986)-173131. With this embodiment wherein a single nozzle is used, the mechanism is simplified, operation failures decrease, and the cost decreases.

Also, with the aforesaid embodiment wherein the opening 111a of the tank 111 containing the reference solution 110 is made as small as to allow insertion of the pipe 95 thereinto, evaporation and deterioration of the reference solution 110 can be prevented as compared with the case where the reference solution 110 is kept to stand in the sample cups 80, 80, . . . at the accommodating regions 40, 40, . . . as in the case of the liquid sample. Furthermore, with the substantially large tank 111, no replenishment of the reference solution 110 thereto is required for a long period.

Operations of the embodiment of the biochemical analysis apparatus in accordance with the present invention shown in FIG. 1 will be described hereinbelow. It is ordinarily practiced that a monitor means for monitoring the operating condition is provided on the apparatus 1, thereby automatically carrying out processing such as stop of the apparatus 1 and issuance of a warning to the operator in the case of abnormal operation. Therefore, processing in the case of abnormal operation will be only briefly described below.

First, the power source switch of the apparatus 1 is turned on by the operator to supply electric power to the apparatus 1 only after the necessary test film has been accommodated in the apparatus 1. In the case where the power switch is off and the test film is present in the test film accommodating means 12, the cooling and dehumidifying device 58 is kept energized to maintain the inside of the refrigerator 50 at a predetermined temperature and humidity.

After the electric power is supplied to the apparatus 1, initial setting of the apparatus 1 is carried out in the sequence described below. Specifically, in the case where the sample application means 5 is not at its upper position, it is moved to its upper position by the movement means 17. The sample application means 5 is then moved by the movement means 17 to a predetermined end of the rail 16.

Thereafter, the sample application means 5 is moved by the movement means 17 toward the washing region 18, and is stopped by a signal received from a position detection means (not shown) for producing the signal at the time the sample application means 5 arrives at the washing region 18. On the other hand, by way of example, a pulse encoder (not shown) is provided on a shaft of a motor (not shown) for moving the sample application means 5 along the rail 16. The pulses produced by the pulse encoder in proportion to the amount of rotation of the motor are counted during the movement of the sample application means 5 from the predetermined end of the rail 16 to the washing region 18. Based on the number of the pulses counted, the presence or absence of slipping between the shaft of the motor and the movement of the sample application means 5 along the rail 16 is detected.

The positions of the pistons 124 and 125 shown in FIG. 8 are monitored to detect whether they are or are not at their start positions that make the space 98 and the space 109 smallest. In the case where the pistons 124 and 125 are not at their start positions, the motors 116 and 120 are rotated in the directions as indicated by the arrows J and L, respectively, to move the pistons 124 and 125 to their start positions. At this time, the solenoid valve 99 is controlled so that the pipes 90 and 94 communicate with each other. In the case where there has been liquid remaining in, for example, the space 109 in the cylinder 108, the liquid is delivered from the leading edge 15a of the sample applying nozzle 15 to the washing region 18 via the pipe 43.

The shutter 54 shown in FIG. 3 and the shutter 69 shown in FIG. 6 are monitored to detect whether they are present at the positions closing the incubators 55 and 68, and the inside of the incubator 55 and the inside of the incubator 68 are maintained at the predetermined temperature.

Also, monitor is effected to detect whether, for example, the levels of the reference solution 110 and the washing liquid 113 in the tanks 111 and 114 are or are not higher than the predetermined levels, and whether the measuring device 70 and the slide conveyance means 65 are or are not at their waiting positions. Then, issuance of a warning to the operator when necessary and automatic shifting to the initial condition are carried out.

After the apparatus 1 has been set to the initial condition in the manner described above, the completion of the initial setting is indicated to the operator.

Thereafter, the operator pours the liquid sample which need not be centrifuged into the sample cup 80 and places it at a predetermined position in the sample accommodating means 4. Body fluid requiring centrifugation is poured into the sample cup 80', and the sample cup 80' is placed at a predetermined position in the centrifugation means 6. The information on the measuring item for the liquid sample (body fluid) is entered from the keyboard 22 or from a floppy disk storing the information inserted into the floppy disk drive unit 25. The apparatus 1 automatically detects whether the test film corresponding to the measuring item thus specified has been or has not been accommodated in the test film accommodating means 12. Also, the position of the liquid sample (body fluid) in the sample accommodating means 4 (centrifugation means 6) is entered to the apparatus 1 from, for example, the keyboard 22. In the case where measurement is to be carried out for a plurality of the liquid samples (body fluids), the aforesaid operations are repeated.

Thereafter, a measurement start instruction is given by the operator to the apparatus 1 by use of, for example, the keyboard 22, and the automatic measuring operations are started.

First, in the case where the body fluid samples have been accommodated at the centrifugation means 6, centrifugation is carried out by the operations of the motors 83, 85 and the clutches 84, 86. After the centrifugation, the body liquid samples (liquid samples) are located one after another at the liquid sample take-out position 42a in the sequence of measurement.

In the case where the liquid samples have been accommodated at the sample accommodating means 4, they are located one after another at the liquid sample take-out position 40a in the sequence of measurement.

Thereafter, the sample application means 5 positioned at the washing region 18 in the initial condition is moved to suck the liquid sample from the sample accommodating means 4 or the centrifugation means 6 into the pipes 43, 44 and 90 by broadening the space 98 in the cylinder 97 while the level of the liquid sample is monitored by means of the liquid level detector 45. In the case where a plurality of measurements are to be carried out, in order to complete suction of the liquid sample by a single operation and shorten the overall measurement time, the liquid sample is sucked in an amount sufficient for all measurements. At this time, the pipes 43, 44 and 90 have often been filled with the washing liquid by the washing operation as will be described later. Therefore, before the liquid sample is thus sucked, air is slightly sucked into the pipe 43 with the leading edge 15a of the sample applying nozzle 15 present in air, and the leading edge 15a of the sample applying nozzle 15 is then entered into the liquid sample. As a result, an air layer intervenes between the washing liquid and the sucked liquid sample so that they do not mix together.

Then, the sample application means 5 is moved up and moved along the rail 16 to the sample applying position on the test film specified in advance. The case where the liquid sample is applied onto the long test film 3 and the case where it is applied onto the slide 30 will hereinbelow be described separately.

First, in the case where the liquid sample is to be applied to the long test film 3, sample application to the long test film 3 is first carried out even though sample application to the slide 30 is necessary, thereby to shorten the overall measurement time. As described above with reference to FIG. 5, sample application to the long test film 3 is carried out by the operations of the shutter 54 and the upper cover 55a of the incubator 55. In order to minimize deterioration of the long test film 3 with the passage of time, the long test film 3 is pulled out of the film feed cassette 7 by the test film conveyance means exactly prior to the sample application.

In the case where the liquid sample is to be applied to a plurality of the long test films 3, 3, . . . , in order to minimize the movement of the sample application means 5 and shorten the overall measurement time, the sample application is basically carried out sequentially from the long test film 3 accommodated at an end among the long test films 3, 3, . . . toward the one at the other end. However, in the case where the measurement sequence is specified by the operator when, for example, measurement results of a measurement item are to be investigated urgently, the sample application is carried out in the specified sequence.

After the liquid sample has been applied to the long test film 3, the long test film 3 is incubated, and the optical density at the portion applied with the liquid sample is measured. The measurement results are fed to the computer 20, necessary calculation processing is carried out, and the results of calculation processing are stored and fed out.

Sample application to the slide 30, when necessary, is carried out as described below.

In the case where sample application is to be carried out for both the slide 30 and the long test film 3, sample application to the long test film 3 is first carried out in the manner as mentioned above, and then the sample application means 5 is moved to the sample applying position 41' of the slide 30, and the liquid sample is applied to the slide 30 in the manner as mentioned above. As in the case of the long test film 3, in order to prevent deterioration of the slide 30, conveyance of the slide 30 from the refrigerator 50 to the predetermined position by the slide conveyance member 65 is carried out exactly prior to the sample application to the slide 30. After the liquid sample has been applied to the slide 30, the sample application means 5 is moved to the nozzle washing region 18. A small vessel (not shown) is placed at the nozzle washing region 18. By way of example, distilled water is contained in the vessel and is made to run so that fresh distilled water is always contained in the vessel. After being moved to the nozzle washing region 18, the sample application means 5 is moved down by the movement means 17 until the leading edge 15a of the sample applying nozzle 15 enters the distilled water.

During the movement of the sample application means 5, the reference solution 110 is accumulated in the cylinder 108 shown in FIG. 8 by the above-mentioned operations. After the leading edge 15a of the sample applying nozzle 15 has been entered to the distilled water, the liquid sample remaining in the pipe 43 and other pipes is delivered from the leading edge 15a of the sample applying nozzle 15. In the case where the pipe 90 and other pipes have been filled with the washing liquid, the washing liquid is then delivered. Also, the reference solution 110 which has slightly been mixed with the washing liquid in the pipe 90 and other pipes is delivered. As a result, the reference solution 110 is filled in the pipes up to the leading edge 15a of the sample applying nozzle 15.

The reference solution 110 is then applied to the predetermined on the slide 30. The reference solution 110 should be applied to the slide 30 as early as possible (for example, within 3 seconds) after the liquid sample has been applied to the slide 30, and therefore the application of the liquid sample to the slide 30 is carried out after the sample application to the necessary long test film 3 has been finished. With this procedure, when sample application is necessary for both the long test film 3 and the slide 30, take-out of the liquid sample from the sample accommodating means 4 or the centrifugation means 6 can be completed by a single operation, and the overall measurement time can be shortened. The measurement time for the slide 30 ($Na^+$, $K^+$, $Cl^-$ potential difference measurement item) is approximately one minute, whereas the measurement time for the long test film 3 (color reaction) is approximately four minutes on the average. Therefore, in order to shorten the overall measurement time, measurement for the slide 30 should be carried out last. Also, since the sample applying positions 41' and 41" for the slide 30, the nozzle washing region 18, and the sample accommodating means 4 are provided close to one another, the distance of movement of the sample application means 5 between the step of application of the liquid sample to the slide 30 and the step of application of the reference solution to the slide 30 by the aforesaid operations can be minimized, and the overall measurement time can further be shortened.

The slide 30 on which the liquid sample and the reference solution have already been applied is incubated in the manner as mentioned above, and the difference in potential is measured. The measurement results are fed to the computer 20, necessary calculation processing is carried out, and the results of calculation processing are stored and fed out.

After the sample application is finished in the manner as mentioned above, the sample application means 5 is moved to the nozzle washing region 18, and the leading edge 15a of the sample applying nozzle 15 is immersed in distilled water. Thereafter, the pistons 124 and 125 shown in FIG. 8 are moved to their start positions if they were not there, and the liquid sample, the reference solution and the like are delivered from the leading edge 15a of the sample applying nozzle 15. The washing liquid is then accumulated in the cylinder 108 by the above-mentioned operations, and delivered from the leading edge 15a of the sample applying nozzle 15 for the purpose of washing.

In the case where the liquid sample which is to be determined next is still present in the sample accommodating means 4 or the centrifugation means 6 after the aforesaid operations have been finished, the liquid sample is moved to the liquid sample take-out position 40a or 42a, and the aforesaid operations are repeated.

Figure 9:
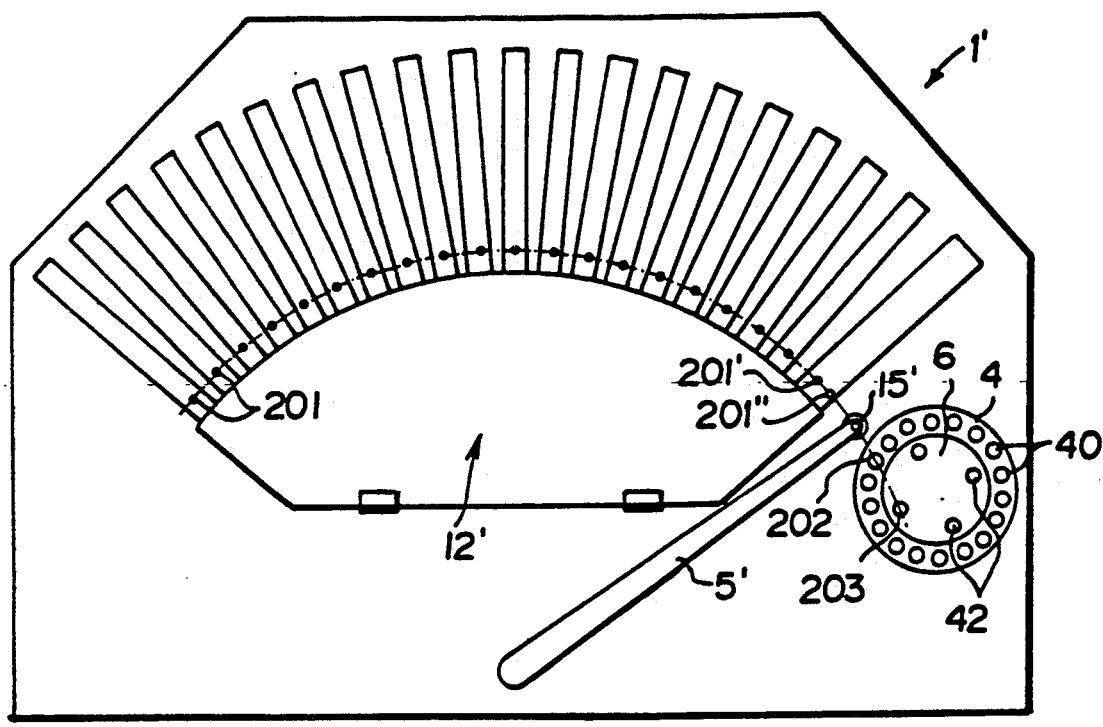
FIG. 9 is a plan view showing another embodiment of the biochemical analysis apparatus in accordance with the present invention.

FIG. 9 shows another embodiment of the biochemical analysis apparatus in accordance with the present invention.

With reference to FIG. 9, a biochemical analysis apparatus 1' is different from the aforesaid apparatus 1 in that a sample applying nozzle 15' of a sample application means 5' is moveable along a circular arc path indicated by 201, . . . , 201' and 202" for all test films pulled or pushed out of a test film accommodating means 12', a liquid sample take-out position 202 of the sample accommodating means 4, and a liquid sample take-out position 203 of the centrifugation means 6 are disposed in the circular arc path.

With the arrangement in the circular arc path, as in the case of the aforesaid embodiment employing the arrangement on the straight line, the configuration of a movement means (not shown) for rotating the sample application means 5' can be simplified, failures of the apparatus 1' can be minimized, and the cost thereof can be reduced.

Figure 10:
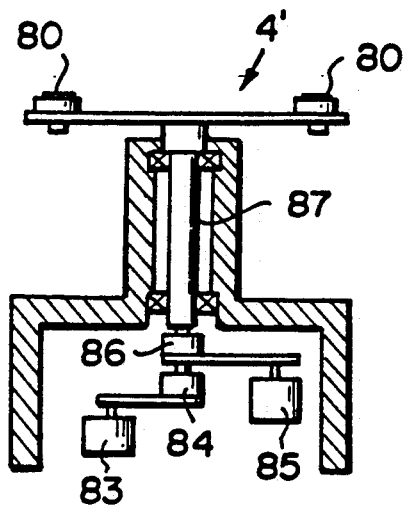
FIG. 10 is a sectional view showing the sample accommodating means provided with a centrifuging function.

FIG. 10 shows a sample accommodating means 4' provided with the centrifuging function.

In the aforesaid embodiment, as shown in FIG. 7, the sample accommodating means 4 is disposed outward from the centrifugation means 6. Instead, in the embodiment shown in FIG. 10, the sample accommodating means 4' accommodates both the liquid sample and the body fluid, and is provided with the centrifuging function for preparing the liquid sample by centrifuging the body fluid accommodated in the sample accommodating means 4'. In FIG. 10, similar elements are numbered with the same reference numerals with respect to FIG. 7. With this embodiment, the configuration becomes simpler, failures of the apparatus can be decreased to a higher extent and the cost thereof can further be reduced than in the case where the sample accommodating means 4 and the centrifugation means 6 are disposed as shown in FIG. 7.

Figure 11:
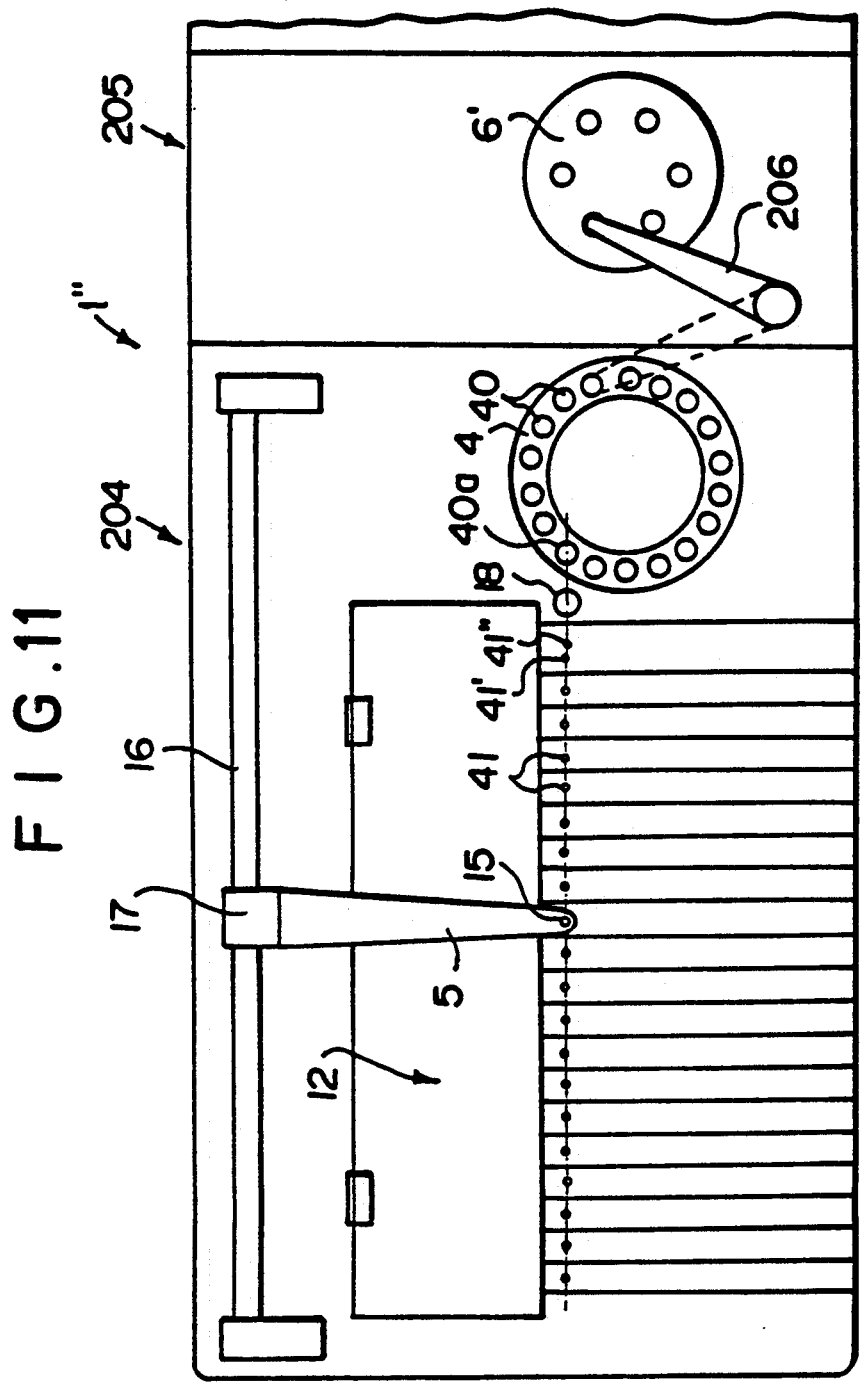
FIG. 11 is a plan view showing a further embodiment of the biochemical analysis apparatus in accordance with the present invention.

FIG. 11 shows a further embodiment of the biochemical analysis apparatus in accordance with the present invention. In this embodiment, instead of providing a centrifugation means 6' inward from the sample accommodating means 4, an apparatus 1" is constituted so that it is dividable into an analysis unit 204 and a centrifugation unit 205.

By way of example, the analysis unit 204 and the centrifugation unit 205 stand side by side as shown in FIG. 11, the body fluid after centrifugation (liquid sample) is transferred by a sample transfer means 206 from the centrifugation means 6' to the sample accommodating means 4. Transfer of the liquid sample may be carried out by taking up the liquid sample by use of the same configuration as the sample application means 5. Alternatively, sample cups of the same type for containing the liquid sample (body fluid) may be used at the centrifugation means 6' and the sample accommodating means 4, and the liquid sample may be transferred together with the sample cup from the centrifugation means 6' to the sample accommodating means 4.

After the liquid sample has been transferred as mentioned above, measurement is carried out in the same manner as in the case where no liquid sample (body fluid) is placed at the centrifugation means 6 in the aforesaid embodiment.

With the apparatus 1" dividable into the analysis unit 204 and the centrifugation unit 205, in the case where only a liquid sample requiring no centrifugation is to be analyzed or a centrifugal separator is already present, analysis can be carried out by use of the analysis unit 204 alone. Therefore, the apparatus 1" is advantageous from the viewpoint of economics. In the case where the centrifugation unit 205 is provided as shown in FIG. 11, the analysis unit 204 and the centrifugation unit 205 can be operated integrally by the aid of the sample transfer means 206.

The aforesaid embodiments of the biochemical analysis apparatus in accordance with the present invention are constituted for carrying out both the measurement of a change in the optical density by use of the long test film 3 and the measurement of a difference in potential by use of the slide. However, the function of measuring the difference in potential may be provided when necessary, and the biochemical analysis apparatus may be constituted for carrying out only the measurement of a change in the optical density by use of the long test film 3.

In the aforesaid embodiments, a plurality of items can be measured by accommodating a plurality of the long test films 3, 3, . . . The biochemical analysis apparatus in accordance with the present invention may also be constituted for accommodating only a single long test film 3.

An embodiment of the first refrigerator for a biochemical analysis apparatus in accordance with the present invention will hereinbelow be described with reference to FIGS. 12 to 19.

Figure 12:
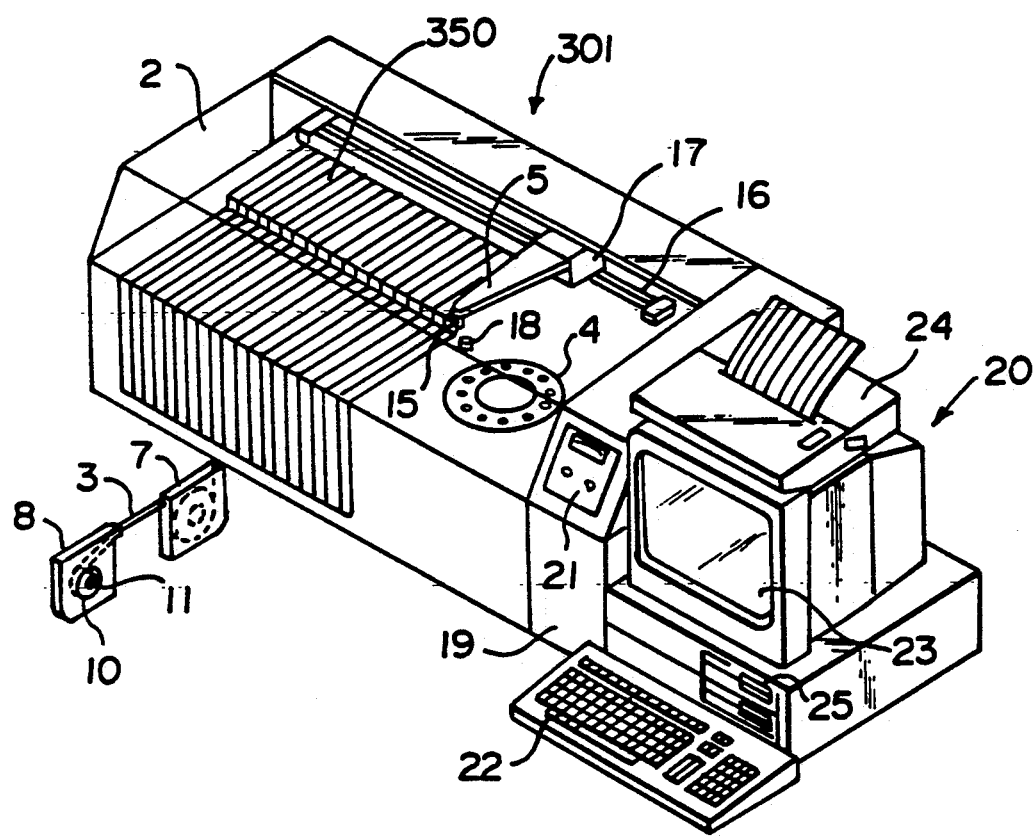
FIG. 12 is a perspective view showing an embodiment of the biochemical analysis apparatus for colorimetry provided with the first refrigerator for a biochemical analysis apparatus in accordance with the present invention.

FIG. 12 shows a biochemical analysis apparatus 301 for colorimetry provided with a refrigerator 350 as the test film accommodating means. In FIG. 12, similar elements are numbered with the same reference numerals with respect to FIG. 1.

Figure 13:
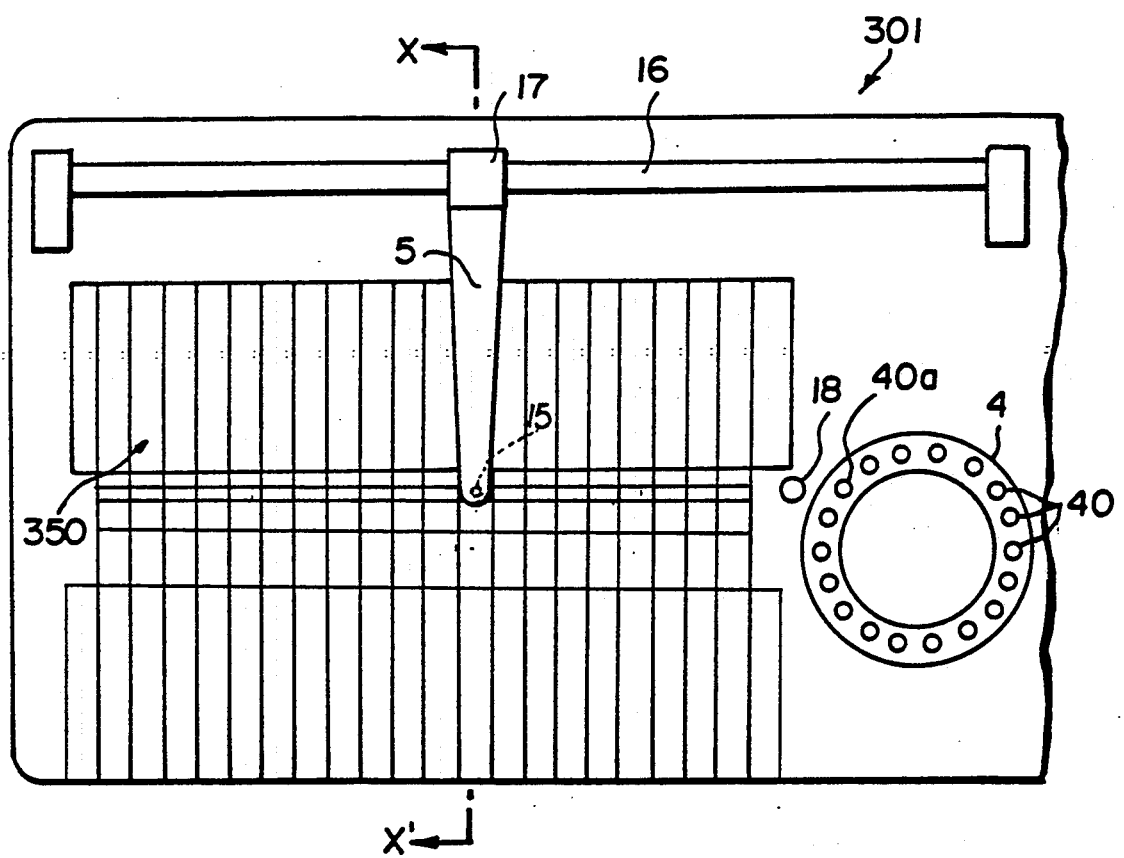
FIG. 13 is a plan view showing the major part of the biochemical analysis apparatus shown in FIG. 12.

FIG. 13 shows the major part of the biochemical analysis apparatus shown in FIG. 12. In FIG. 13, similar elements are numbered with the same reference numerals with respect to FIG. 2.

Figure 14:
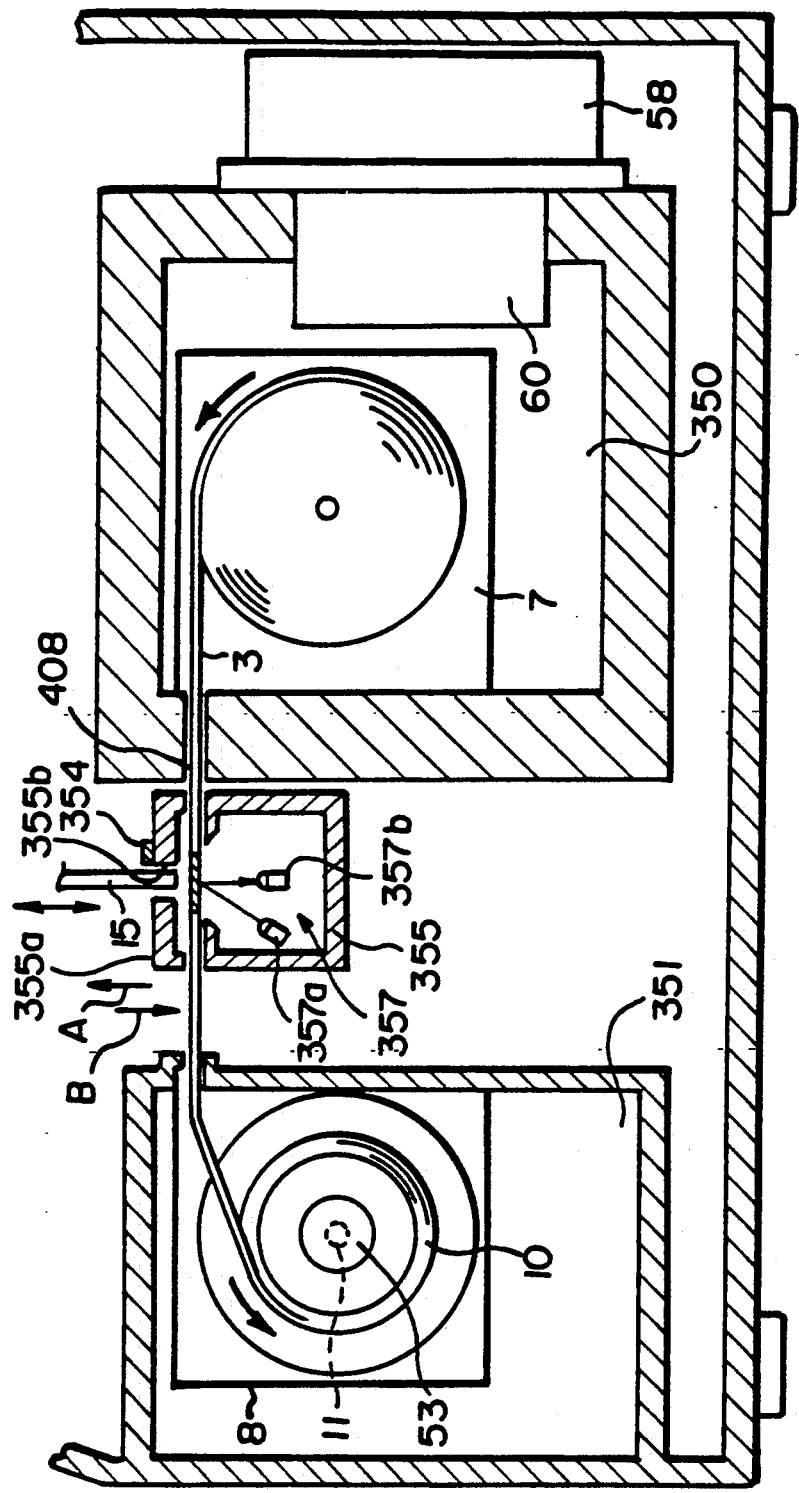
FIG. 14 is a sectional view taken along line X—X' of FIG. 13.

FIG. 14 shows the sectional configuration along line X—X' of FIG. 13. In FIG. 14, similar elements are numbered with the same reference numerals with respect to FIG. 3. In FIG. 14, the inside of the refrigerator 350 is adjusted to, for example, 4° C.

An incubator 355 capable of holding the long test film 3 therein and allowing it to pass therethrough sequentially is provided at the position where the long test film 3 is exposed between the film feed cassette 7 and the film wind-up cassette 8. A measuring device 357 for measuring the optical density given rise to by the color reaction of the long test film 3 with the liquid sample is provided inside of the incubator 355.

As the motor 53 is rotated, the long test film 3 is intermittently pulled out of the refrigerator 350 leftward in FIG. 14. An upper cover 355a of the incubator 355 is moved up as indicated by the arrow A before the long test film 3 is thus fed out, and is moved down as indicated by the arrow B to push down the long test film 3 after the long test film 3 has thus been moved. Then, a shutter 354 which has closed a nozzle insertion hole 355b of the upper cover 355a is moved rightward, and the sample applying nozzle 15 is moved down to apply the liquid sample onto the long test film 3 through the nozzle insertion hole 355b. The shutter 354 is then moved leftward to close the nozzle insertion hole 355b and prevent air flow between the inside and outside of the incubator 355. The area in the incubator 355 is thus maintained at a predetermined temperature (for example, 37° C.), and the sample-applied portion of the long test film 3 indicated by hatching in FIG. 14 is maintained at the predetermined for a predetermined time (for example, four minutes) in the incubator 355. During or after the incubation, the optical density of the sample-applied portion of the long test film 3 is measured by a measuring device 357. The measurement is carried out by irradiating light produced by a light irradiating means 357a and having a wavelength selected in advance to the sample-applied portion of the long test film 3, and detecting the light reflected by the sample-applied portion by use of a photodetector 357b.

After the application of the aforesaid liquid sample, incubation and measurement are finished in this manner, next sample application becomes possible. The long test film 3 is maintained in the incubator 355 after the measurement has been finished, and is then moved exactly prior to the sample application for the next analysis until the film portion which is to be used for the next analysis is disposed at the sample applying position.

Figure 15:
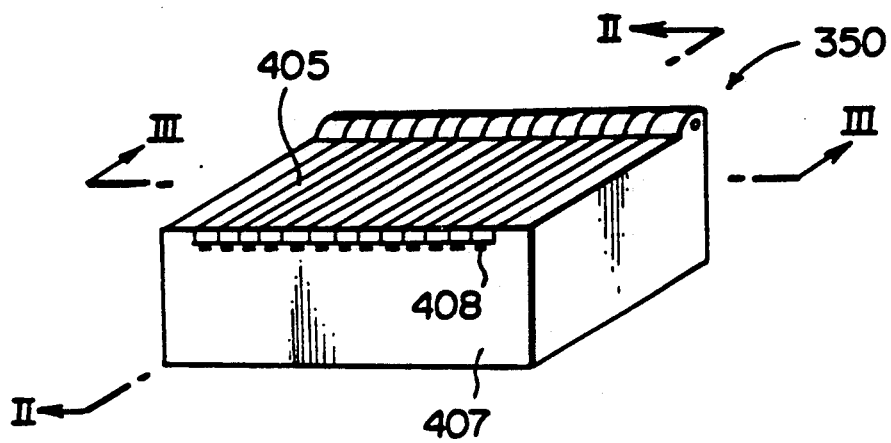
FIG. 15 is a perspective view showing an embodiment of the first refrigerator for a biochemical analysis apparatus in accordance with the present invention.
Figure 16:
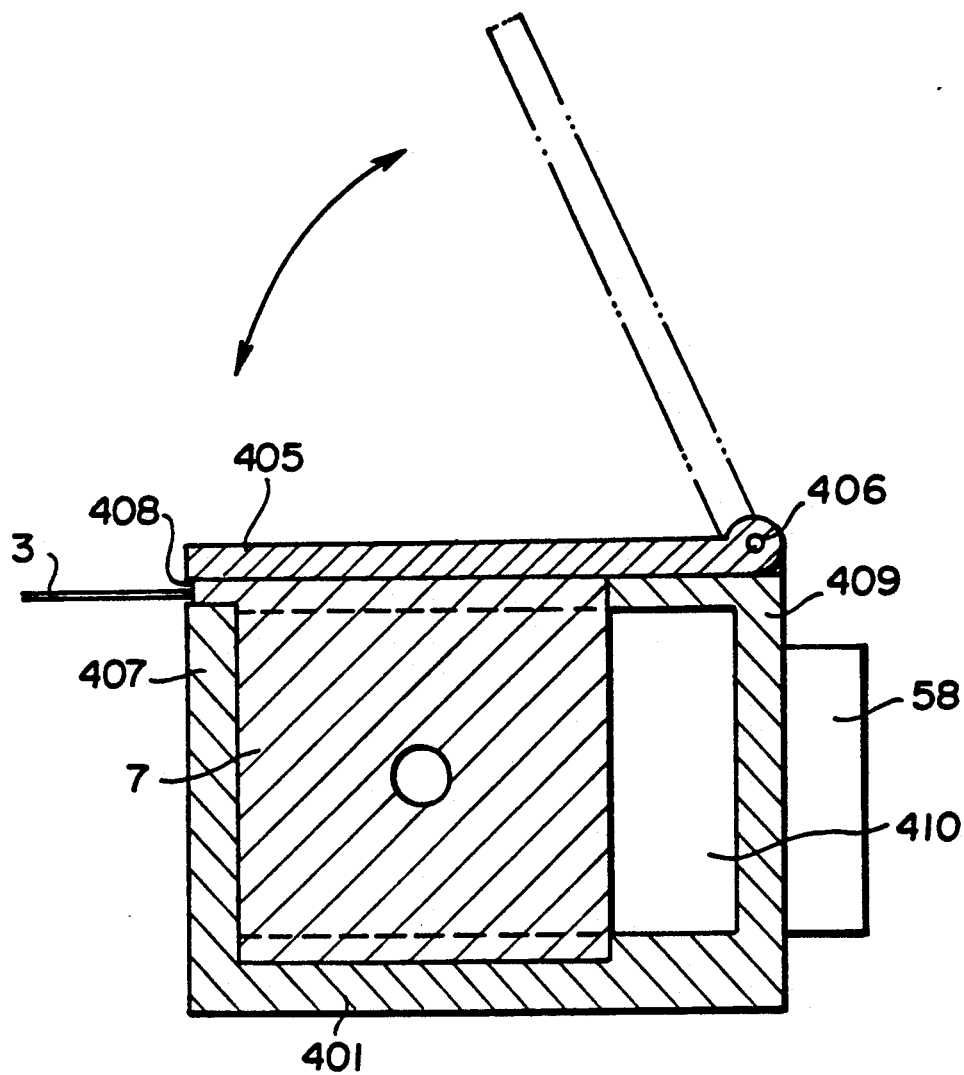
FIG. 16 is a sectional view taken along line II—II of FIG. 15.
Figure 17:
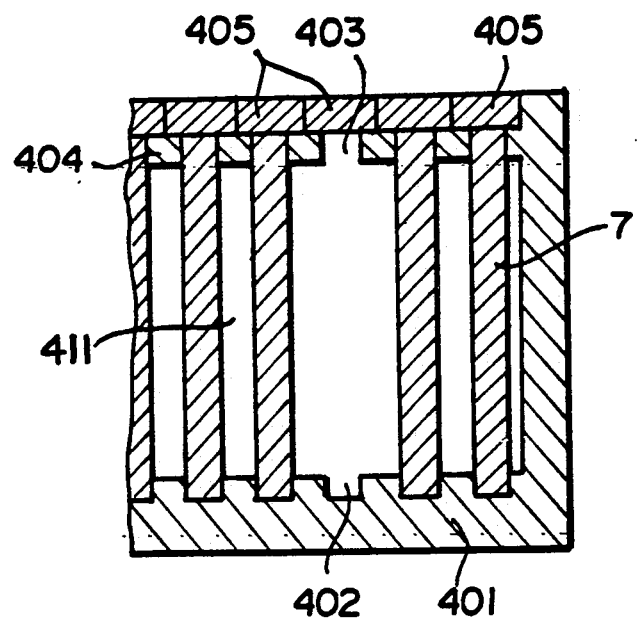
FIG. 17 is a sectional view taken along line III—III of FIG. 15.

FIG. 15 is a perspective view showing an embodiment of the first refrigerator for a biochemical analysis apparatus in accordance with the present invention, FIG. 16 is a sectional view taken along line II—II of FIG. 15, and FIG. 17 is a sectional view taken along line III—III of FIG. 15. With reference to FIGS. 15, 16 and 17, a plurality of the film feed cassettes 7, 7, ... are accommodated upright in the refrigerator 350 so that they stand in parallel in the horizontal direction in FIG. 15 with the flat side surfaces facing each other.

Figure 18:
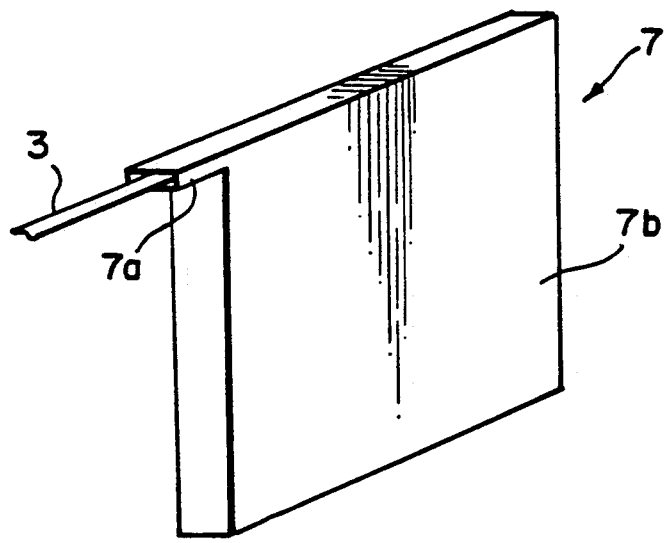
FIG. 18 is a perspective view showing an example of the film feed cassette accommodated in the refrigerator for a biochemical analysis apparatus in accordance with the present invention.

FIG. 18 shows an example of the film feed cassette 7. With reference to FIG. 18, the film feed cassette 7 has a nearly square side surface 7b, and is constituted by a thick-walled, hollow, rectangular parallelopiped case having a thickness slightly larger than the width of the long test film 3. The long test film 3 is housed in the roll form in the cassette case, and a film outlet portion 7a is protruded from the case body.

The cassette case can be fabricated by a known method. For example, the box-like member and the cover of the cassette case may be made independently, and thereafter secured to each other by fitting, engagement, fixing with screws, adhesion and any other means after the unused long test film has been accommodated in the box-like member. Alternatively, the box-like member and the cover may be coupled by a hinge on one side of the cover.

In the case where the long test film 3 is wound up in a too small curvature radius, it will crack. Therefore, the diameter of the reel (not shown in FIG. 18) around which the long test film 3 is to be wound up in the film feed cassette 7 should not be so small. In general, the diameter should preferably be within the range of 40 mm to 80 mm. Also, an engagement member for wind-up and stop of the long test film 3 are provided inside of the reel.

In general, the cassette case and the reel can be easily made from various thermoplastic resins, for example, polyolefin resins such as polyethylene and polypropylene, styrene resins such as polystyrene, high-impact polystyrene, a styrene-acrylonitrile resin and an ABS resin, a polyvinyl chloride resin, nylon, polyester, polycarbonate, polyacetal and other resins by utilizing the technique ordinarily used for making audio or video cassette tapes.

Figure 19:
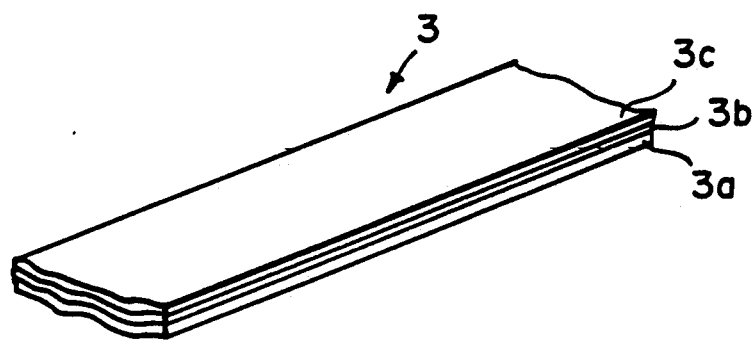
FIG. 19 is a perspective view showing an example of the long test film.

By way of example, as shown in FIG. 19, the long test film 3 is a colorimetric analysis test film having multi-layer analysis elements. With reference to FIG. 19, the colorimetric analysis test film 3 comprises a light-permeable support 3a, a reagent layer 3b overlaid on the support 3a, and a spreading layer 3c overlaid on the reagent layer 3b. In biochemical analysis, the liquid sample is applied onto the spreading layer 3c, and is allowed to spread therethrough. An analysis objective constituent of the liquid sample migrates to the reagent layer 3b, and reacts with the reagent contained in the reagent layer 3b. A change in color density produced by the color reaction of the analysis objective constituent with the reagent is measured by irradiating light from the side of the support 3a and measuring the light reflected by the colorimetric analysis test film 3, thereby to analyze the analysis objective constituent contained in the liquid sample based on the principle of colorimetry. The colorimetric analysis test film 3 may also be provided with other layers known in the art such as a reflection layer, a light-shielding layer, a filter layer, a registration layer, a water absorbing layer and a prime coat layer. Also, the spreading layer 3c and the reagent layer 3b may be constituted by a single layer.

The configuration of the multi-layer analysis element shown in FIG. 19 is already known.

By way of example, the support 3a is constituted by a film of a light-permeable, water-impervious material, for example, a polymer such as polyethylene terephthalate, bisphenol-A polycarbonate, polystyrene, or a cellulose ester (e.g. cellulose diacetate, cellulose triacetate, or cellulose acetate propionate). The thickness of the support 3a should preferably be within the range of approximately 50 $\mu$m to approximately 300 $\mu$m, more preferably within the range of 80 $\mu$m to 200 $\mu$m. The width of the support 3a should preferably be within the range of approximately 3 mm to 10 mm. The length of the support 3a may be selected in accordance with the number of analyses per roll, which is not limited particularly. In general, it is advantageous that the length of the support 3a be equivalent to 100 to 600 analysis regions.

The spreading layer 3c horizontally spreads the liquid sample applied to the surface thereof approximately at a predetermined rate per unit area substantially without maldistribution of the constituent contained in the liquid sample. The spreading layer 3c is formed of a paper such as a filter paper, or a knitted, woven or non-woven fabric of a natural fiber or a synthetic fiber. Also, the spreading layer 3c may be constituted by a porous material of a particulate polymer.

In order to control spreading of the liquid sample, the spreading layer 3c may also contain a hydrophilic polymer such as a cellulose derivative, polyvinyl pyrrolidone, polyvinyl alcohol or polyacrylamide, a surface active agent such as a nonionic surface active agent, a cationic surface active agent, an anionic surface active agent or an amphoteric surface active agent, and/or a buffer suitable for achieving analysis reliably.

The reagent layer 3b contains a reagent suitable for producing a change in color density detectable with colorimetry upon reaction with the analysis objective constituent. The reagent layer 3b should preferably be prepared by dispersing at least one kind of reagent in a hydrophilic colloid (as a binder) of, for example, gelatin, a gelatin derivative, polyvinyl alcohol, polyacrylamide, or polyvinyl pyrrolidone.

Another example of the long test film 3 is a test film provided with sheet-like ion selective electrodes for measuring the ionic activity of a liquid sample by applying the liquid sample and a reference solution respectively to ion selective layers of the ion selective electrodes, which ion selective layers are electrically isolated from each other, and measuring a difference in potential between the ion selective electrodes.

Reverting to FIGS. 15, 16 and 17, walls (i.e. side walls and a bottom wall) outside of the upper surface of the refrigerator 350 have a heat insulating structure which may be of a known type. For example, the overall walls outside of the upper surface of the refrigerator 350 may be formed integrally by use of a heat insulating material, or may be of a double-wall structure with the hollow space inside thereof being filled with a heat insulating material.

The inner surface of a bottom wall 401 is provided with grooves 402, 402, ... into which the bottoms of the film feed cassettes 7, 7, ... are to be fitted when the film feed cassettes 7, 7, ... are accommodated upright in the refrigerator 350. The grooves 402, 402, ... are provided in a number equal to the number of the film feed cassettes 7, 7, ... accommodated in the refrigerator 350. The width of each grove 402 should preferably be nearly equal to the thickness of the film feed cassette 7 so that the film feed cassette 7 does not move substantially in the horizontal direction in the groove 402. The length of the groove 402 should preferably be nearly equal to the length of the bottom of the film feed cassette 7 so that the film feed cassette 7 does not move substantially in the horizontal direction in the groove 402. In general, ten to thirty cassettes 7, 7, ... are accommodated in the refrigerator 350. However, the number of the cassettes 7, 7, ... accommodated is not limited.

A support plate 404 having through holes 403, 403, ... parallel to the flat side surfaces of the film feed cassettes 7, 7, ... is provided at the upper part of the refrigerator 350. Each of the through holes 403, 403, ... has a size allowing the passage of the film feed cassette 7 therethrough and supports the film feed cassette 7 by the hole edge faces. The support plate 404 should preferably be provided so that the refrigerator 350 is open to the exterior only at the through holes 403, 403, ... The width and the length of each through hole 403 should preferably be adjusted so that the film feed cassette 7 does not move substantially in the horizontal direction. Also, the support plate 404 should preferably be provided so that the upper surface thereof is flush with the upper edge face of the film feed cassette 7 with the film feed cassette 7 fitted in the groove 402.

Covers 405, 405, ... for covering the through holes 403, 403, ... and openable independently around a shaft 406 are provided on the support plate 404. The covers 405, 405, ... are close to one another and cover the upper surface of the refrigerator 350 as a whole. As in the case of the walls, the covers 405, 405, ... have a heat insulating structure. Film outlet holes 408, 408, ... into which the film outlet portions 7a, 7a, ... of the film feed cassettes 7, 7, ... are to be inserted are provided at the upper edge of a side wall 407 of the refrigerator 350. The long test films 3, 3, ... are respectively pulled out of the film outlet portions 7a, 7a, ...

The cooling and dehumidifying device 58 for cooling and dehumidifying air in the refrigerator 350 is provided outside of a side wall 409 facing the side wall 407. A space 410 is formed between the side wall 409 and the film feed cassettes 7, 7, ..., and air can flow freely between the space 410 and gaps 411, 411, ... among the film feed cassettes 7, 7, ... By way of example, a fan (not shown) is provided at the space 410 for circulating air in the refrigerator 350 and uniformly maintaining all of the film feed cassettes 7, 7, ... at a low temperature and low humidity.

With the refrigerator 350 having the aforesaid configuration, the inside of the refrigerator 350 is substantially airtight, and air in the refrigerator 350 can be maintained at a low temperature and low humidity. When one of the film feed cassettes 7, 7, ... is to be exchanged with a new one, only the cover 405 at the film feed cassette 7 which is to be exchanged can be opened. Therefore, entry of ambient air into the refrigerator 350 can be minimized, and an increase of the temperature and humidity in the refrigerator 350 can thus be minimized. Also, with the configuration wherein the film feed cassettes 7, 7, ... are fitted to the grooves 402, 402, ... and the through holes 403, 403, ... so that the cassettes 7, 7, ... do not move substantially, the gaps 411, 411, ... are nearly independent of one another. Therefore, when one of the covers 405, 405, ... is opened, the film feed cassettes 7, 7, ... outside of the cassette 7 at which the cover 405 is opened are not adversely affected by a change in temperature and humidity of internal air caused by ambient air entering from the through hole 403 at which the cover 405 is opened. Accordingly, analysis results can be obtained accurately and reliably.

Instead of providing a single cover 405 for each of the film feed cassette 7, a single cover 405 may be provided for a group of an arbitrary number of the film feed cassettes 7, 7, ..., for example, for a group of two or three film feed cassettes 7, 7, ... Also, the covers 405, 405, ... may be provided for groups composed of different numbers of the film feed cassettes 7, 7, ...

Also, a single cover (not shown) for covering the overall upper surface of the refrigerator 350 may be provided on the covers 405, 405, ..., thereby to form a double cover configuration at the upper surface of the refrigerator 350.

Instead of providing the covers 405, 405, ... as shown in FIG. 16 so that they can be rotatably opened and closed around the shaft 406, they may be mounted on the upper edge of the side wall 409 openably and closeably by hinges, or may be opened and closed by horizontal sliding movements in FIG. 15.

An embodiment of the second refrigerator for a biochemical analysis apparatus in accordance with the present invention will hereinbelow be described with reference to FIGS. 20 to 26.

Figure 20:
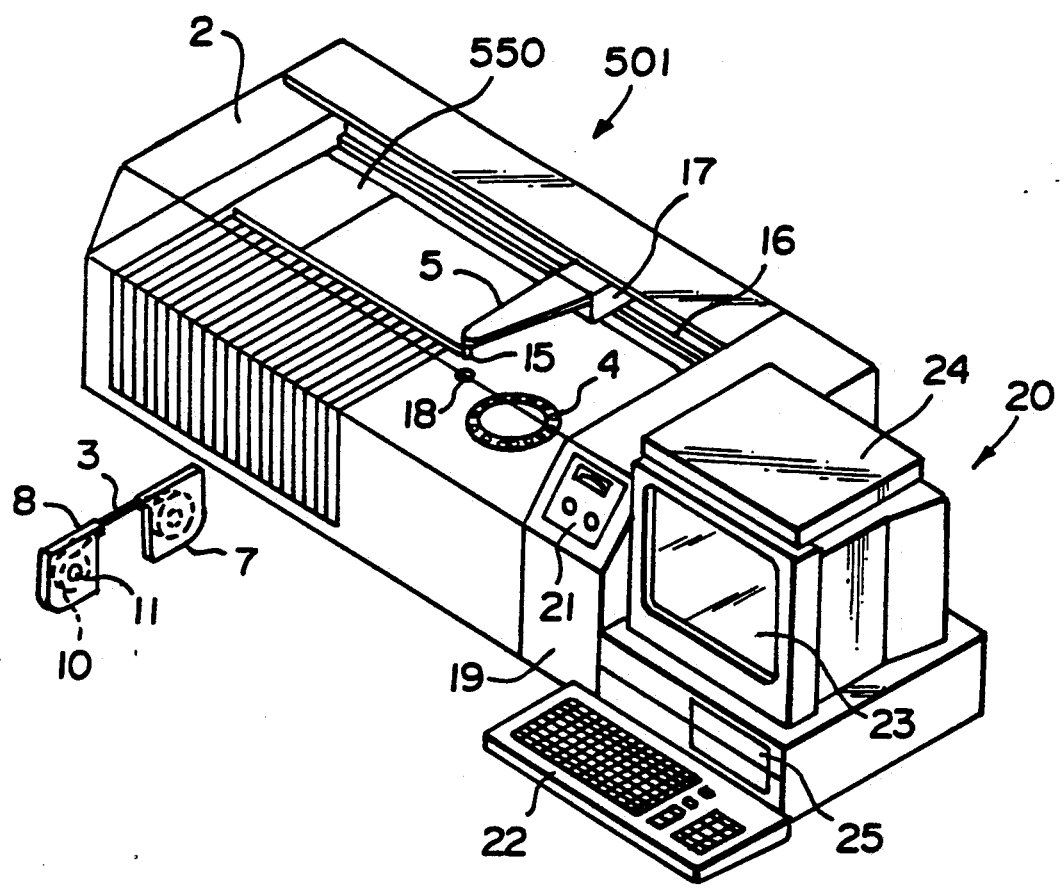
FIG. 20 is a perspective view showing an embodiment of the biochemical analysis apparatus for colorimetry provided with the second refrigerator for a biochemical analysis apparatus in accordance with the present invention.

FIG. 20 shows a biochemical analysis apparatus 501 for colorimetry provided with a refrigerator 550 as the test film accommodating means. In FIG. 20, similar elements are numbered with the same reference numerals with respect to FIG. 1.

Figure 21:
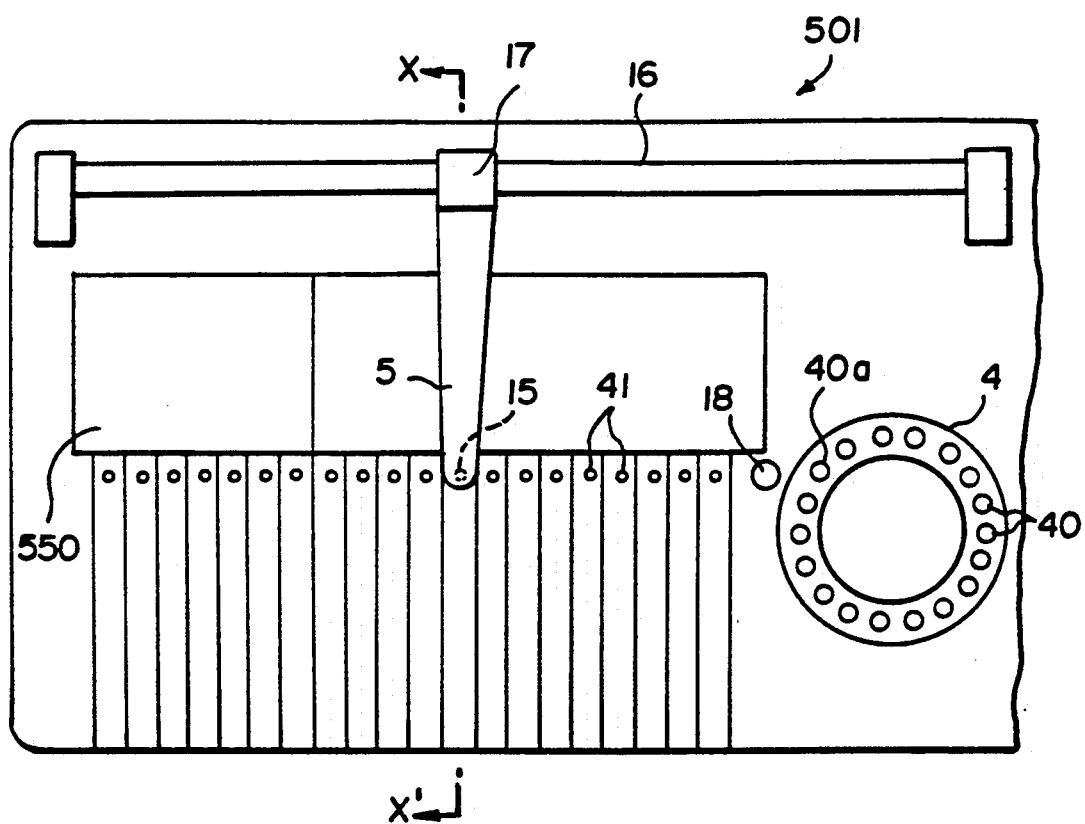
FIG. 21 is a plan view showing the major part of the biochemical analysis apparatus shown in FIG. 20.

FIG. 21 shows the major part of the biochemical analysis apparatus shown in FIG. 20. In FIG. 21, similar elements are numbered with the same reference numerals with respect to FIG. 2. The sectional configuration taken along line X—X' of FIG. 21 is the same as that shown in FIG. 14.

Figure 22:
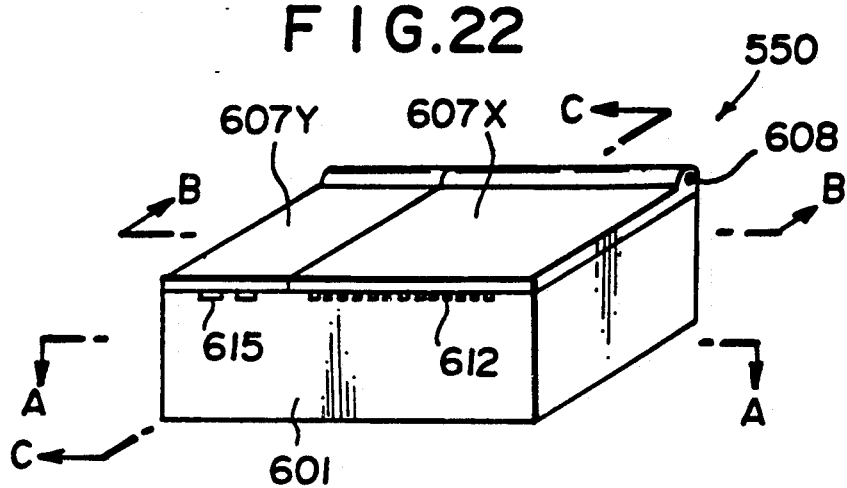
FIG. 22 is a perspective view showing an embodiment of the second refrigerator for a biochemical analysis apparatus in accordance with the present invention.
Figure 23:
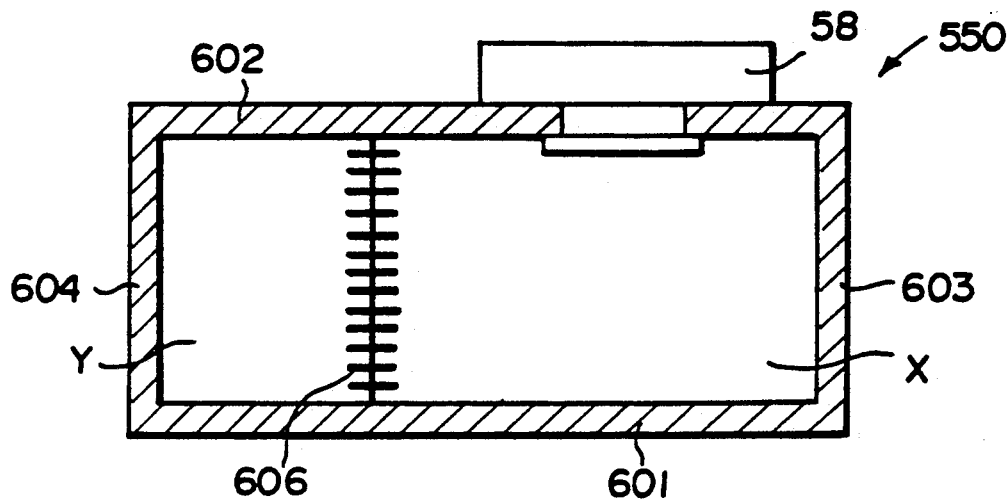
FIG. 23 is a sectional view taken along line A—A of FIG. 22.
Figure 24:
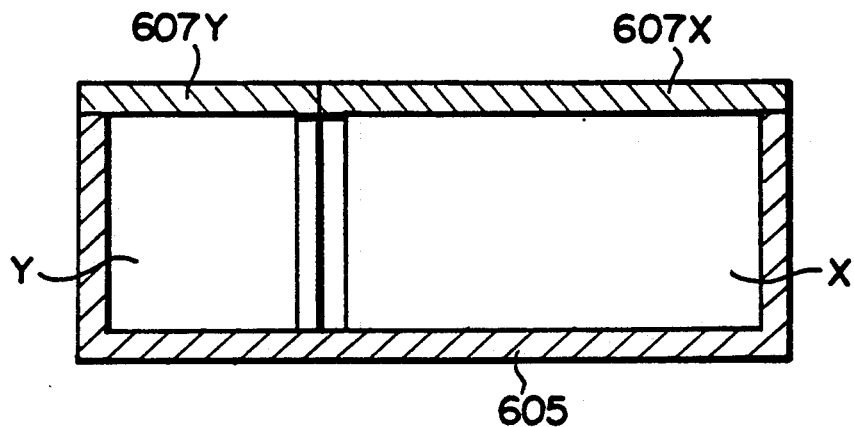
FIG. 24 is a sectional view taken along line B—B of FIG. 22.
Figure 25:
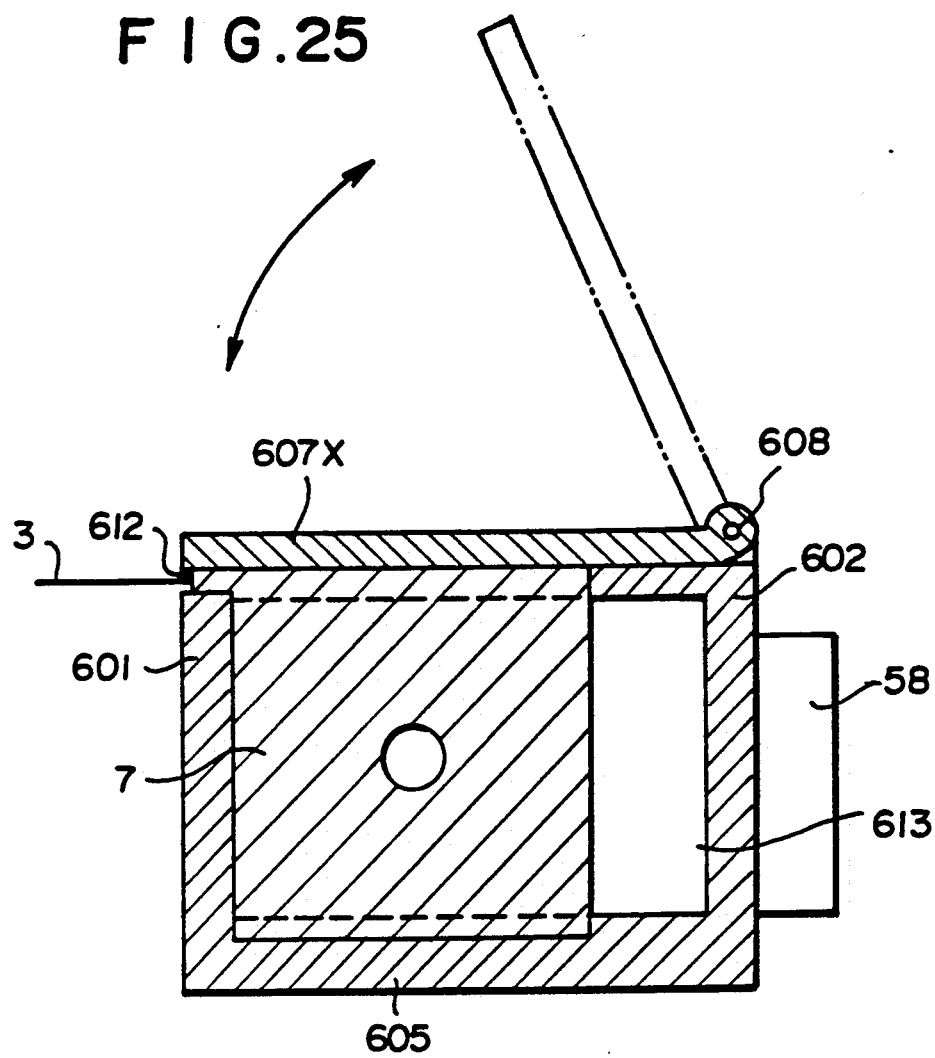
FIG. 25 is an enlarged sectional view taken long line C—C of FIG. 22.
Figure 26:
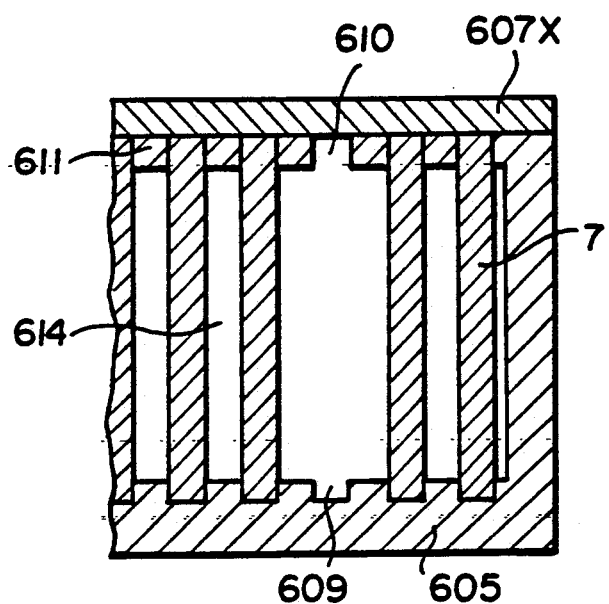
FIG. 26 is an enlarged sectional view taken long line B—B of FIG. 22.

FIG. 22 is a perspective view showing an embodiment of the second refrigerator for a biochemical analysis apparatus in accordance with the present invention, FIG. 23 is a sectional view taken along line A—A of FIG. 22, and FIG. 24 is a sectional view taken along line B—B of FIG. 22. FIG. 25 is an enlarged sectional view taken along line C—C of FIG. 22, and FIG. 26 is an enlarged sectional view taken along line B—B of FIG. 22.

With reference to FIGS. 22, 23 and 24, walls (i.e. a front side wall 601, a rear side wall 602, a right side wall 603, a left side wall 604 and a bottom wall 605) outside of the upper surface of the refrigerator 550 have a heat insulating structure. The area inside of the refrigerator 550 is divided by a partition wall 606 into compartments X and Y, and covers 607X and 607Y having a heat insulating structure and divided from each other for covering the compartments X and Y are provided at the upper surface of the refrigerator 550. The covers 607X and 607Y cover the overall upper surface of the refrigerator 550.

The heat insulating structure may be of a known type. For example, the overall walls outside of the upper surface of the refrigerator 550 may be formed integrally by use of a heat insulating material, or may be of a double-wall structure with the hollow space inside thereof being filled with a heat insulating material.

The compartment X is directly cooled by the cooling and dehumidifying device 58 provided on the rear side wall 602. The compartment Y is cooled by the partition wall 606 which is cooled by the temperature in the compartment X. The compartment X is suitable for accommodating the long test films or slides for biochemical analysis which are sensitive to temperature and humidity and which should be maintained at a lower temperature and lower humidity. The compartment Y is suitable for accommodating the long test films or slides for biochemical analysis which are less susceptible to effects of temperature and humidity.

The partition wall 606 achieves heat exchange between air in the compartment X and air in the compartment Y, and has a structure having a large heat transfer area, for example, a fin structure or a corrugated structure, made of a material exhibiting a high thermal conductivity such as copper, aluminium, magnesium or zinc. The material and the structure of the partition wall 606 may be selected in accordance with the properties of the long test films or the slides which are to be accommodated in the compartments X and Y. In general, the partition wall 606 should preferably be provided so that air does not flow between the compartments X and Y. However, the partition wall 606 may be provided with small holes for increasing the cooling rate of the compartment Y, depending on the kinds of and relationship between the long test films and the slides accommodated in the compartments X and Y.

With the refrigerator 550 having the aforesaid configuration, the compartments X and Y are independent of each other and substantially airtight, and the temperature and humidity in the compartment X do not change when the cassettes or cartridges in the compartment Y are exchanged.

Instead of providing the covers 607X and 607Y one for each of the compartments X and Y, the covers 607X and 607Y may be divided into two or more cover members.

Also, a single cover (not shown) for covering the overall upper surface of the refrigerator 550 may be provided on the covers 607X and 607Y, thereby to form a double cover configuration at the upper surface of the refrigerator 550.

Instead of providing the covers 607X and 607Y as shown in FIG. 25 so that they can be rotatably opened and closed around a shaft 608, they may be mounted on the upper edge of the side wall 602 openably and closeably by hinges, or may be opened and closed by vertical sliding movements in FIG. 23.

Two or more partition walls 606, 606, ... may be provided in the refrigerator 550 to partition the refrigerator 550 into three or more compartments. In this case, the compartments Y, Y cooled by cool air in the compartment X may be provided on both sides of the compartment X directly cooled by the cooling and dehumidifying device 58. Also, the compartments in a number within the range of two to less than the total number may be cooled directly by the cooling and dehumidifying device 58.

Also, instead of providing the cooling and dehumidifying device 58 at the refrigerator 550, the cooling and dehumidifying device 58 may be provided at the biochemical analysis apparatus 501, and the compartment of the refrigerator 550 which is to be cooled may be cooled by an appropriate means.

An example of accommodation of the film feed cassettes 7, 7, ... in the refrigerator 550 will now be described in detail with reference to FIGS. 25 and 26. A plurality of the film feed cassettes 7, 7, ... are accommodated upright in the compartment X so that they stand in parallel in the horizontal direction in FIG. 22 with the flat side surfaces facing each other.

The inner surface of the bottom wall 605 is provided with grooves 609, 609, ... into which the bottoms of the film feed cassettes 7, 7, ... are to be fitted when the film feed cassettes 7, 7, ... are accommodated upright in the compartment X. The grooves 609, 609, ... are provided in a number equal to the number of the film feed cassettes 7, 7, ... accommodated in the compartment X. The width of each grove 609 should preferably be nearly equal to the thickness of the film feed cassette 7 so that the film feed cassette 7 does not move substantially in the horizontal direction in the groove 609. The length of the groove 609 should preferably be nearly equal to the length of the bottom of the film feed cassette 7 so that the film feed cassette 7 does not move substantially in the horizontal direction in the groove 609. In general, ten to thirty cassettes 7, 7, ... are accommodated in the compartment X. However, the number of the cassettes 7, 7, ... accommodated is not limited.

A support plate 611 having through holes 610, 610, ... parallel to the flat side surfaces of the film feed cassettes 7, 7, ... is provided at the upper part of the compartment X. Each of the through holes 610, 610, ... has a size allowing the passage of the film feed cassette 7 therethrough and supports the film feed cassette 7 by the hole edge faces. The support plate 611 should preferably be provided so that the compartment X is open to the exterior only at the through holes 610, 610, ... The width and the length of each through hole 610 should preferably be adjusted so that the film feed cassette 7 does not move substantially in the horizontal direction. Also, the support plate 611 should preferably be provided so that the upper surface thereof is flush with the upper edge face of the film feed cassette 7 with the film feed cassette 7 fitted in the groove 609.

The cover 607X is provided on the support plate 611. The cover 607X may be divided into cover members each for covering a single through hole 610 or an arbitrary number of (for example, two or three) through holes 610, 610, . . . In this case, the cover members may be provided openable independently of each other around the shaft 608. The cover members are provided close to one another to cover the upper surface of .the compartment X as a whole. Film outlet holes 612, 612, . . . into which the film outlet portions 7a, 7a, . . . of the film feed cassettes 7, 7, . . . as shown in FIG. 18 are to be inserted are provided at the upper edge of the front side wall 601 of the refrigerator 550. The long test films 3, 3, . . . are respectively pulled out of the film outlet portions 7a, 7a, . . .

The cooling and dehumidifying device 58 for cooling and dehumidifying air in the compartment X is provided outside of the rear side wall 602. A space 613 is formed between the side wall 602 and the film feed cassettes 7, 7, . . . in the compartment X, and air can flow freely between the space 613 and gaps 614, 614, . . . among the film feed cassettes 7, 7, . . . By way of example, a fan (not shown) is provided at the space 613 for circulating air in the compartment X and uniformly maintaining all of the film feed cassettes 7, 7, . . . at a low temperature and low humidity.

With the configuration wherein the film feed cassettes 7, 7, . . . are fitted to the grooves 609, 609, . . . and the through holes 613, 613, . . . so that the cassettes 7, 7, . . . do not move substantially, the gaps 614, 614, . . . are nearly independent of one another. In the case where the cover 607X is divided into cover members each for covering a single through hole 610, even though one of the cover members is opened, the film feed cassettes 7, 7, . . . outside of the cassette 7 at which the cover member is opened are not adversely affected by a change in temperature and humidity of internal air caused by ambient air entering from the through hole 610 at which the cover member is opened. Accordingly, analysis results can be obtained accurately and reliably.

Also, the cartridges housing the ion selective electrode slides are accommodated in the compartment Y so that the slides can be taken out through outlet holes 615, 615.

We claim:

1. A biochemical analysis apparatus comprising:
   i) a sample accommodating means for accommodating a liquid sample,
   ii) a test film accommodating means for accommodating a plurality of long test films, each of said long test film containing a reagent which reacts with said liquid sample to give rise to a change in optical density, and controlling an unused length of each of said long test films at a predetermined temperature and humidity so that deterioration of each of said long test films is controlled,
   iii) a test film conveyance means for sequentially pulling out each of said long test films accommodated in said test film accommodating means,
   iv) a sample application means for taking up said liquid sample accommodated in said sample accommodating means and sequentially applying a predetermined amount of said liquid sample onto a portion of each of said long test films at the position to which each of said long test films has been pulled out sequentially of said test film accommodating means,
   v) an incubator for maintaining the portion of each of said long test films, having said predetermined amount of said liquid sample applied thereon by said sample application means, at a predetermined temperature for a predetermined time, and
   iv) a detection means for irradiating light to said portion of each of said long test films, having said predetermined amount of said liquid sample applied thereon, and measuring the optical density given rise to by a reagent-sample reaction during or after the passage of said predetermined time.

2. A biochemical analysis apparatus as defined in claim 1 wherein said test film accommodating means and said incubator are disposed close to each other.

3. A biochemical analysis apparatus as defined in claim 1 wherein said test film conveyance means is constructed so as to pull out each of said long test film from said test film accommodating means exactly before the sample application is carried out.

4. A biochemical analysis apparatus as defined in claim 1, wherein said test film accommodating means included a refrigerator accommodating in a parallel row a plurality of cassettes housing said plurality of long test films for biochemical analysis, said refrigerator comprising:
   i) a main body having a heat insulating configuration, and
   ii) a plurality of cover members divided from one another in the direction of the row of said cassettes, said cover members being openable and closeable independently of one another and having heat insulating configurations, said cover members being coupled to said main body.

5. A biochemical analysis apparatus as defined in claim 4 wherein said cover members are provided one for each of said cassettes.

6. A biochemical analysis apparatus as defined in claim 4 wherein said cover members are provided one for an arbitrary number of said cassettes.

7. A biochemical analysis apparatus as defined in claim 4 wherein each of said cover members is supported at one of its edge portions rotatably with respect to said main body.

8. A biochemical analysis apparatus as defined in claim 4 wherein said cover members are openable and closeable by being horizontally slideable with respect to said main body.

9. A biochemical analysis apparatus as defined in claim 1, wherein said test film accommodating means includes a refrigerator accommodating in a parallel row a plurality of cassettes housing said plurality of long test films for biochemical analysis said refrigerator comprising:
   i) outer walls having a heat insulating configuration,
   ii) at least one partition wall having large heat transfer effects partitioning the area surrounded by said outer walls into at least two compartments, and
   iii) a cooling means associated with at least one of said compartments.

10. A biochemical analysis apparatus as defined in claim 9 wherein a cover having a heat insulating configuration is provided on an upper surface of said refrigerator.

11. A biochemical analysis apparatus as defined in claim 10 wherein said cover comprises a plurality of cover members which correspond in number to at best the number of said compartments.

12. A biochemical analysis apparatus as defined in claim 9 wherein said cooling means is positioned and arranged so as to cool said at least one compartment and the other of said at least two compartments is cooled by said at least one partition wall allowing the cooling effect of said cooling means to be transferred thereto.

13. A biochemical analysis apparatus comprising:
  i) a sample accommodating means for accommodating a liquid sample,
  ii) an analysis slide accommodating means for accommodating a plurality of cartridges, each cartridge housing a plurality of biochemical analysis slides, each of said biochemical analysis slides containing a reagent which reacts with said liquid sample to give rise to a change in optical density, and controlling a number of unused biochemical analysis slides in said cartridges at a predetermined temperature and humidity so that deterioration of each of said unused biochemical analysis slides is controlled,
  iii) an analysis slide conveyance means for sequentially conveying each of said biochemical analysis slides accommodated in said analysis slide accommodating means,
  iv) a sample application means for taking up said liquid sample accommodated in said sample accommodating means and sequentially applying a predetermined amount of said liquid sample onto a portion of each of said biochemical analysis slides at the position to which each of said biochemical analysis slides have been conveyed sequentially from said analysis slide accommodating means,
  v) an incubator for maintaining the portion of each of said biochemical analysis slides having said predetermined amount of said liquid sample applied thereon by said sample application means, at a predetermined temperature for a predetermined time, and
  vi) a detection means for irradiating light to said portion of each of said biochemical analysis slides having said predetermined amount of said liquid sample applied thereon, and measuring the optical density given rise to by a reagent-sample reaction during or after the passage of said predetermined time,
  wherein said analysis slide accommodating means includes a refrigerator accommodating in a parallel row a plurality of said cartridges housing biochemical analysis slides, said refrigerator comprising:
  i) outer walls having a heat insulating configuration,
  ii) at least one partition wall having large heat transfer effects partitioning the area surrounded by said outer walls into at least two compartments, and
  iii) a cooling means associated with at least one of said compartments.

* * * * *